(12) United States Patent
Shalev

(10) Patent No.: US 9,839,510 B2
(45) Date of Patent: Dec. 12, 2017

(54) STENT-GRAFTS WITH POST-DEPLOYMENT VARIABLE RADIAL DISPLACEMENT

(75) Inventor: Alon Shalev, Ra'anana (IL)

(73) Assignee: ENDOSPAN LTD., Herzilyia Pituach (IL)

( * ) Notice: Subject to any disclaimer, the term of this patent is extended or adjusted under 35 U.S.C. 154(b) by 167 days.

(21) Appl. No.: 14/240,600

(22) PCT Filed: Apr. 4, 2012

(86) PCT No.: PCT/IL2012/000148
§ 371 (c)(1),
(2), (4) Date: May 13, 2014

(87) PCT Pub. No.: WO2013/030818
PCT Pub. Date: Mar. 7, 2013

(65) Prior Publication Data
US 2014/0324154 A1    Oct. 30, 2014

Related U.S. Application Data

(60) Provisional application No. 61/528,242, filed on Aug. 28, 2011, provisional application No. 61/553,209, filed on Oct. 30, 2011.

(51) Int. Cl.
*A61F 2/04*    (2013.01)
*A61F 2/07*    (2013.01)
(Continued)

(52) U.S. Cl.
CPC .................. *A61F 2/07* (2013.01); *A61F 2/82* (2013.01); *A61F 2/89* (2013.01);
(Continued)

(58) Field of Classification Search
CPC ........ A61F 2/07; A61F 2/90; A61F 2002/075; A61F 2/958; A61F 2210/0004;
(Continued)

(56) References Cited

U.S. PATENT DOCUMENTS 4,180,613 A   12/1979  Vassiliou
4,355,426 A   10/1982  MacGregor
(Continued)

FOREIGN PATENT DOCUMENTS

CA    2497704     3/2004
CN    2453960    10/2001
(Continued)

OTHER PUBLICATIONS

Communication dated Jul. 2, 2014 from the State Intellectual Property Office of the P.R.C. in counterpart application No. 201080062714.5.
(Continued)

*Primary Examiner* — Ann Schillinger
(74) *Attorney, Agent, or Firm* — Sughrue Mion, PLLC

(57) ABSTRACT

An endovascular stent-graft includes a generally tubular body configured to assume a radially-compressed delivery state and a radially-expanded deployment state. The body includes a flexible stent member, and a tubular fluid flow guide attached to the stent member. The body includes a compliance-restoration body portion extending axially along a portion of the body, and including portions of the stent member and fluid flow guide. When the body is in the radially-expanded deployment state, the compliance-restoration body portion characterized by a greatest diastolic outer radius when the body is internally pressurized by fluid having a pressure of 80 mmHg, and radially expandable to a greatest systolic outer radius when the body is internally pressurized by fluid having a pressure of 120 mmHg. The greatest systolic outer radius ($R_S$) is at least 5% greater than the greatest diastolic outer radius.

18 Claims, 13 Drawing Sheets

(51) Int. Cl.
  *A61F 2/82* (2013.01)
  *A61F 2/06* (2013.01)
  *A61F 2/89* (2013.01)

(52) U.S. Cl.
  CPC ... *A61F 2002/065* (2013.01); *A61F 2002/075* (2013.01); *A61F 2210/0057* (2013.01); *A61F 2210/0066* (2013.01); *A61F 2220/0075* (2013.01); *A61F 2230/0078* (2013.01); *A61F 2250/001* (2013.01); *A61F 2250/0007* (2013.01); *A61F 2250/0013* (2013.01); *A61F 2250/0039* (2013.01)

(58) Field of Classification Search
  CPC ...... A61F 2210/0014; A61F 2210/0076; A61F 2230/0069; A61F 2250/0067; A61F 2/82; A61F 2002/065; A61F 2002/823; A61F 2/915; A61F 2002/077; A61F 2002/30062
  See application file for complete search history.

(56) References Cited

U.S. PATENT DOCUMENTS

| | | |
|---|---|---|
| 4,505,767 A | 3/1985 | Quin |
| 4,562,596 A | 1/1986 | Kornberg |
| 4,577,631 A | 3/1986 | Kreamer |
| 4,617,932 A | 10/1986 | Kornberg |
| 4,665,906 A | 5/1987 | Jervis |
| 4,739,762 A | 4/1988 | Palmaz |
| 4,787,899 A | 11/1988 | Lazarus |
| 4,816,339 A | 3/1989 | Tu et al. |
| 4,878,906 A | 11/1989 | Lindemann et al. |
| 4,886,062 A | 12/1989 | Wiktor |
| 4,938,740 A | 7/1990 | Melbin |
| 4,969,458 A | 11/1990 | Wiktor |
| 5,042,707 A | 8/1991 | Taheri |
| 5,064,435 A | 11/1991 | Porter |
| 5,104,404 A | 4/1992 | Wolff |
| 5,122,136 A | 6/1992 | Guglielmi et al. |
| 5,133,732 A | 7/1992 | Wiktor |
| 5,192,256 A | 3/1993 | Ryan |
| 5,192,286 A | 3/1993 | Phan et al. |
| 5,234,448 A | 8/1993 | Wholey et al. |
| 5,383,926 A | 1/1995 | Lock et al. |
| 5,456,694 A | 10/1995 | Marin et al. |
| 5,486,183 A | 1/1996 | Middleman et al. |
| 5,507,769 A | 4/1996 | Marin et al. |
| 5,509,923 A | 4/1996 | Middleman et al. |
| 5,522,880 A | 6/1996 | Barone et al. |
| 5,527,322 A | 6/1996 | Klein et al. |
| 5,549,662 A | 8/1996 | Fordenbacher |
| 5,554,181 A | 9/1996 | Das |
| 5,556,413 A | 9/1996 | Lam |
| 5,562,724 A | 10/1996 | Vorwerk et al. |
| 5,607,445 A | 3/1997 | Summers |
| 5,613,974 A | 3/1997 | Andreas et al. |
| 5,632,746 A | 5/1997 | Middleman et al. |
| 5,632,763 A | 5/1997 | Glastra |
| 5,632,772 A | 5/1997 | Alcime et al. |
| 5,639,278 A | 6/1997 | Dereume et al. |
| 5,643,340 A | 7/1997 | Nunokawa |
| 5,653,743 A | 8/1997 | Martin |
| 5,676,696 A | 10/1997 | Marcade |
| 5,676,697 A | 10/1997 | McDonald |
| 5,693,084 A | 12/1997 | Chuter |
| 5,728,134 A | 3/1998 | Barak |
| 5,749,879 A | 5/1998 | Middleman et al. |
| 5,755,770 A | 5/1998 | Ravenscroft |
| 5,755,771 A | 5/1998 | Penn et al. |
| 5,755,774 A * | 5/1998 | Pinchuk .................. 623/1.13 |
| 5,755,777 A | 5/1998 | Chuter |
| 5,755,781 A | 5/1998 | Jayaraman |
| 5,769,882 A | 6/1998 | Fogarty et al. |
| 5,769,884 A | 6/1998 | Solovay |
| 5,782,903 A | 7/1998 | Wiktor |
| 5,782,906 A | 7/1998 | Marshall et al. |
| 5,824,040 A | 10/1998 | Cox et al. |
| 5,824,055 A | 10/1998 | Spiridigliozzi et al. |
| 5,827,321 A | 10/1998 | Roubin et al. |
| 5,843,170 A | 12/1998 | Ahn |
| 5,855,600 A | 1/1999 | Alt |
| 5,860,991 A | 1/1999 | Klein et al. |
| 5,876,432 A | 3/1999 | Lau et al. |
| 5,906,641 A | 5/1999 | Thompson et al. |
| 5,921,994 A | 7/1999 | Andreas et al. |
| 5,925,076 A | 7/1999 | Inoue |
| 5,948,018 A | 9/1999 | Dereume et al. |
| 5,968,091 A | 10/1999 | Pinchuk et al. |
| 5,976,178 A | 11/1999 | Goldsteen et al. |
| 5,980,552 A | 11/1999 | Pinchasik et al. |
| 5,984,955 A | 11/1999 | Wisselink |
| 6,015,431 A | 1/2000 | Thornton et al. |
| 6,016,810 A | 1/2000 | Ravenscroft |
| 6,030,414 A | 2/2000 | Taheri |
| 6,033,435 A | 3/2000 | Penn et al. |
| 6,036,723 A | 3/2000 | Anidjar et al. |
| 6,036,725 A | 3/2000 | Avellanet |
| 6,049,824 A | 4/2000 | Simonin |
| 6,051,021 A | 4/2000 | Frid |
| 6,059,824 A | 5/2000 | Taheri |
| 6,077,298 A | 6/2000 | Tu et al. |
| 6,099,497 A | 8/2000 | Adams et al. |
| 6,099,548 A | 8/2000 | Taheri |
| 6,117,145 A | 9/2000 | Wood et al. |
| 6,129,738 A | 10/2000 | Lashinski et al. |
| 6,132,457 A | 10/2000 | Chobotov |
| 6,152,956 A | 11/2000 | Pierce |
| 6,156,064 A | 12/2000 | Chouinard |
| 6,159,228 A | 12/2000 | Frid et al. |
| 6,168,615 B1 | 1/2001 | Ken et al. |
| 6,176,875 B1 | 1/2001 | Lenker et al. |
| 6,179,878 B1 | 1/2001 | Duerig et al. |
| 6,200,339 B1 | 3/2001 | Leschinsky et al. |
| 6,206,893 B1 | 3/2001 | Klein et al. |
| 6,270,524 B1 | 8/2001 | Kim |
| 6,283,991 B1 | 9/2001 | Cox et al. |
| 6,287,335 B1 | 9/2001 | Drasler et al. |
| 6,290,720 B1 | 9/2001 | Khosravi et al. |
| 6,296,661 B1 | 10/2001 | Davila et al. |
| 6,312,458 B1 | 11/2001 | Golds |
| 6,325,819 B1 | 12/2001 | Pavcnik et al. |
| 6,325,823 B1 | 12/2001 | Horzewski et al. |
| 6,344,056 B1 | 2/2002 | Dehdashtian |
| 6,395,018 B1 | 5/2002 | Castaneda |
| 6,406,420 B1 | 6/2002 | McCarthy et al. |
| 6,428,565 B1 | 8/2002 | Wisselink |
| 6,451,048 B1 | 9/2002 | Berg et al. |
| 6,451,051 B2 | 9/2002 | Drasler et al. |
| 6,471,722 B1 | 10/2002 | Inoue |
| 6,506,211 B1 | 1/2003 | Skubitz et al. |
| 6,520,988 B1 | 2/2003 | Colombo et al. |
| 6,544,279 B1 | 4/2003 | Hopkins et al. |
| 6,565,597 B1 | 5/2003 | Fearnot et al. |
| 6,576,009 B2 | 6/2003 | Ryan et al. |
| 6,613,078 B1 | 9/2003 | Barone |
| 6,635,083 B1 | 10/2003 | Cheng et al. |
| 6,645,242 B1 | 11/2003 | Quinn |
| 6,648,901 B2 | 11/2003 | Fleischman et al. |
| 6,648,911 B1 | 11/2003 | Sirhan et al. |
| 6,652,567 B1 | 11/2003 | Deaton |
| 6,652,571 B1 | 11/2003 | White et al. |
| 6,656,214 B1 | 12/2003 | Fogarty et al. |
| 6,673,080 B2 | 1/2004 | Reynolds et al. |
| 6,692,520 B1 | 2/2004 | Gambale et al. |
| 6,695,833 B1 | 2/2004 | Frantzen |
| 6,695,875 B2 | 2/2004 | Stelter et al. |
| 6,699,277 B1 | 3/2004 | Freidberg et al. |
| 6,716,238 B2 | 4/2004 | Elliott |
| 6,730,117 B1 * | 5/2004 | Tseng et al. .................. 623/1.16 |
| 6,733,523 B2 | 5/2004 | Shaolian et al. |
| 6,743,195 B2 | 6/2004 | Zucker |
| 6,748,953 B2 | 6/2004 | Sherry et al. |
| 6,752,826 B2 | 6/2004 | Holloway et al. |
| 6,776,794 B1 | 8/2004 | Hong et al. |

(56) References Cited

U.S. PATENT DOCUMENTS

| | | |
|---|---|---|
| 6,808,534 B1 | 10/2004 | Escano |
| 6,814,749 B2 | 11/2004 | Cox et al. |
| 6,814,752 B1 | 11/2004 | Chuter |
| 6,824,560 B2 | 11/2004 | Pelton |
| 6,843,803 B2 | 1/2005 | Ryan et al. |
| 6,846,321 B2 | 1/2005 | Zucker |
| 6,860,900 B2 | 3/2005 | Clerc et al. |
| 6,907,285 B2 | 6/2005 | Denker et al. |
| 6,908,477 B2 | 6/2005 | McGuckin, Jr. et al. |
| 6,929,660 B1 | 8/2005 | Ainsworth et al. |
| 6,942,691 B1 | 9/2005 | Chuter |
| 6,953,469 B2 | 10/2005 | Ryan |
| 6,964,679 B1 | 11/2005 | Marcade et al. |
| 6,986,774 B2 | 1/2006 | Middleman et al. |
| 7,008,441 B2 | 3/2006 | Zucker |
| 7,018,400 B2 | 3/2006 | Lashinski et al. |
| 7,022,131 B1 | 4/2006 | Derowe et al. |
| 7,044,962 B2 | 5/2006 | Elliott |
| 7,105,015 B2 | 9/2006 | Goshgarian |
| 7,105,020 B2 | 9/2006 | Greenberg et al. |
| 7,112,217 B1 | 9/2006 | Kugler et al. |
| 7,115,127 B2 | 10/2006 | Lindenbaum et al. |
| 7,122,052 B2 | 10/2006 | Greenhalgh |
| 7,131,991 B2 | 11/2006 | Zarins et al. |
| 7,144,421 B2 | 12/2006 | Carpenter et al. |
| 7,160,318 B2 | 1/2007 | Greenberg et al. |
| 7,175,651 B2 | 2/2007 | Kerr |
| 7,198,638 B2 | 4/2007 | Dong |
| 7,201,772 B2 | 4/2007 | Schwammenthal et al. |
| 7,220,274 B1 | 5/2007 | Quinn |
| 7,223,266 B2 | 5/2007 | Lindenbaum et al. |
| 7,261,733 B1 | 8/2007 | Brown et al. |
| 7,270,675 B2 | 9/2007 | Chun et al. |
| 7,279,003 B2 | 10/2007 | Berra et al. |
| 7,294,145 B2 | 11/2007 | Ward |
| 7,294,147 B2 | 11/2007 | Hartley |
| 7,306,623 B2 | 12/2007 | Watson |
| 7,341,598 B2 | 3/2008 | Davidson et al. |
| 7,393,357 B2 | 7/2008 | Stelter et al. |
| 7,396,363 B2 | 7/2008 | Frid |
| 7,399,313 B2 | 7/2008 | Brown et al. |
| 7,407,509 B2 | 8/2008 | Greenberg et al. |
| 7,413,573 B2 | 8/2008 | Hartley et al. |
| 7,425,219 B2 | 9/2008 | Quadri |
| 7,429,269 B2 | 9/2008 | Schwammenthal et al. |
| 7,438,721 B2 | 10/2008 | Doig et al. |
| 7,442,204 B2 | 10/2008 | Schwammenthal et al. |
| 7,473,272 B2 | 1/2009 | Pryor |
| 7,491,231 B2 | 2/2009 | Nazzaro et al. |
| 7,537,606 B2 | 5/2009 | Hartley et al. |
| 7,537,609 B2 | 5/2009 | Davidson et al. |
| 7,540,881 B2 | 6/2009 | Meyer et al. |
| 7,544,160 B2 | 6/2009 | Gross |
| 7,575,590 B2 | 8/2009 | Watson |
| 7,616,997 B2 | 11/2009 | Kieval et al. |
| 7,637,939 B2 | 12/2009 | Tischler |
| 7,645,298 B2 | 1/2010 | Hartley et al. |
| 7,655,036 B2 | 2/2010 | Goodson |
| 7,655,037 B2 * | 2/2010 | Fleming, III ............ A61F 2/07 623/1.35 |
| 7,662,161 B2 | 2/2010 | Briganti et al. |
| 7,662,168 B2 | 2/2010 | McGuckin, Jr. et al. |
| 7,670,369 B2 | 3/2010 | Schaeffer |
| 7,678,141 B2 | 3/2010 | Greenan et al. |
| 7,699,885 B2 | 4/2010 | Leonhardt et al. |
| 7,708,704 B2 | 5/2010 | Mitelberg et al. |
| 7,722,626 B2 | 5/2010 | Middleman et al. |
| 7,731,732 B2 | 6/2010 | Ken |
| 7,766,955 B2 | 8/2010 | Vardi et al. |
| 7,771,465 B2 | 8/2010 | Zukowski |
| 7,789,903 B2 | 9/2010 | Spiridigliozzi et al. |
| 7,803,178 B2 | 9/2010 | Whirley et al. |
| 7,806,923 B2 | 10/2010 | Moloney |
| 7,815,673 B2 | 10/2010 | Bloom et al. |
| 7,833,259 B2 | 11/2010 | Boatman |
| 7,846,194 B2 | 12/2010 | Hartley et al. |
| 7,850,725 B2 | 12/2010 | Vardi et al. |
| 7,867,270 B2 | 1/2011 | Hartley et al. |
| 7,887,575 B2 | 2/2011 | Kujawski |
| 7,914,572 B2 | 3/2011 | Hartley et al. |
| 7,955,373 B2 | 6/2011 | Sowinski et al. |
| 7,955,374 B2 | 6/2011 | Erickson et al. |
| 7,959,662 B2 | 6/2011 | Erbel et al. |
| 7,959,669 B2 | 6/2011 | Chalekian et al. |
| 7,998,186 B2 | 8/2011 | Hartley |
| 7,998,187 B2 | 8/2011 | Hartley et al. |
| 8,012,193 B2 | 9/2011 | Hartley et al. |
| 8,021,412 B2 | 9/2011 | Hartley et al. |
| 8,021,418 B2 | 9/2011 | Gerberding et al. |
| 8,021,419 B2 | 9/2011 | Hartley et al. |
| 8,043,365 B2 | 10/2011 | Thramann |
| 8,048,139 B2 | 11/2011 | Frid et al. |
| 8,048,140 B2 | 11/2011 | Purdy |
| 8,048,147 B2 | 11/2011 | Adams |
| 8,052,736 B2 | 11/2011 | Doig et al. |
| 8,052,741 B2 | 11/2011 | Bruszewski et al. |
| 8,066,755 B2 | 11/2011 | Zacharias et al. |
| 8,080,026 B2 | 12/2011 | Konstantino et al. |
| 8,080,053 B2 | 12/2011 | Satasiya et al. |
| 8,100,960 B2 | 1/2012 | Bruszewski |
| 8,118,854 B2 | 2/2012 | Bowe |
| 8,133,267 B2 | 3/2012 | Leonhardt et al. |
| 8,157,810 B2 | 4/2012 | Case et al. |
| 8,167,926 B2 | 5/2012 | Hartley et al. |
| 8,172,892 B2 | 5/2012 | Chuter et al. |
| 8,172,895 B2 | 5/2012 | Anderson et al. |
| 8,197,475 B2 | 6/2012 | Bruszewski et al. |
| 8,197,533 B2 | 6/2012 | Kujawski |
| 8,211,158 B2 | 7/2012 | Wolf |
| 8,216,298 B2 | 7/2012 | Wright et al. |
| 8,221,494 B2 | 7/2012 | Schreck et al. |
| 8,226,706 B2 | 7/2012 | Hartley et al. |
| 8,236,040 B2 | 8/2012 | Mayberry et al. |
| 8,251,963 B2 | 8/2012 | Chin et al. |
| 8,257,423 B2 | 9/2012 | Kerr |
| 8,262,719 B2 | 9/2012 | Erickson et al. |
| 8,273,115 B2 | 9/2012 | Hamer et al. |
| 8,287,586 B2 | 10/2012 | Schaeffer et al. |
| 8,292,885 B2 | 10/2012 | Bruszewski et al. |
| 8,292,941 B2 | 10/2012 | Muzslay |
| 8,292,949 B2 | 10/2012 | Berra et al. |
| 8,292,951 B2 | 10/2012 | Muzslay |
| 8,333,800 B2 | 12/2012 | Bruszewski et al. |
| 8,337,546 B2 | 12/2012 | Bruszewski |
| 8,353,898 B2 | 1/2013 | Lutze et al. |
| 8,357,192 B2 | 1/2013 | Mayberry et al. |
| 8,361,134 B2 | 1/2013 | Hartley et al. |
| 8,394,136 B2 | 3/2013 | Hartley et al. |
| 8,425,585 B2 | 4/2013 | Melsheimer et al. |
| 8,470,018 B2 | 6/2013 | Hartley et al. |
| 8,475,513 B2 | 7/2013 | Sithian |
| 8,480,726 B2 | 7/2013 | Cunningham et al. |
| 8,491,646 B2 | 7/2013 | Schreck |
| 8,506,622 B2 | 8/2013 | Bruszewski et al. |
| 2001/0000188 A1 | 4/2001 | Lenker et al. |
| 2001/0004705 A1 | 6/2001 | Killion et al. |
| 2001/0010006 A1 | 7/2001 | Bachinski et al. |
| 2001/0014823 A1 | 8/2001 | Ressemann et al. |
| 2001/0034550 A1 | 10/2001 | Buirge et al. |
| 2001/0037142 A1 | 11/2001 | Stelter et al. |
| 2001/0044647 A1 | 11/2001 | Pinchuk et al. |
| 2001/0044651 A1 | 11/2001 | Steinke et al. |
| 2001/0044652 A1 | 11/2001 | Moore |
| 2001/0047198 A1 | 11/2001 | Drasler et al. |
| 2001/0049550 A1 | 12/2001 | Martin et al. |
| 2001/0053930 A1 | 12/2001 | Kugler et al. |
| 2002/0040236 A1 | 4/2002 | Lau et al. |
| 2002/0052643 A1 | 5/2002 | Wholey et al. |
| 2002/0052644 A1 | 5/2002 | Shaolian et al. |
| 2002/0072790 A1 | 6/2002 | McGuckin, Jr. et al. |
| 2002/0099438 A1 | 7/2002 | Furst |
| 2002/0099441 A1 | 7/2002 | Dehdashtian |
| 2002/0107564 A1 | 8/2002 | Cox et al. |
| 2002/0111667 A1 | 8/2002 | Girton et al. |

(56) References Cited

U.S. PATENT DOCUMENTS

| | | |
|---|---|---|
| 2002/0123791 A1 | 9/2002 | Harrison |
| 2002/0156495 A1 | 10/2002 | Brenneman et al. |
| 2002/0156517 A1 | 10/2002 | Perouse |
| 2002/0173809 A1 | 11/2002 | Fleischman et al. |
| 2002/0183783 A1 | 12/2002 | Shadduck |
| 2002/0193864 A1 | 12/2002 | Khosravi et al. |
| 2002/0198585 A1 | 12/2002 | Wisselink |
| 2003/0033005 A1 | 2/2003 | Houser et al. |
| 2003/0040791 A1 | 2/2003 | Oktay |
| 2003/0057156 A1 | 3/2003 | Peterson et al. |
| 2003/0065386 A1 | 4/2003 | Weadock |
| 2003/0074055 A1 | 4/2003 | Haverkost |
| 2003/0093145 A1 | 5/2003 | Lawrence-Brown et al. |
| 2003/0114061 A1 | 6/2003 | Matsuda et al. |
| 2003/0125796 A1 | 7/2003 | Dong |
| 2003/0130720 A1 | 7/2003 | DePalma et al. |
| 2003/0139802 A1 | 7/2003 | Wulfman et al. |
| 2003/0144725 A1 | 7/2003 | Lombardi |
| 2003/0153944 A1 | 8/2003 | Phung et al. |
| 2003/0153968 A1 | 8/2003 | Geis et al. |
| 2003/0163187 A1 | 8/2003 | Weber |
| 2003/0171771 A1 | 9/2003 | Anderson et al. |
| 2003/0191523 A1 | 10/2003 | Hojeibane |
| 2003/0199967 A1 | 10/2003 | Hartley et al. |
| 2003/0199968 A1 | 10/2003 | Ainsworth et al. |
| 2003/0204236 A1 | 10/2003 | Letort |
| 2003/0204242 A1 | 10/2003 | Zarins et al. |
| 2003/0204243 A1 | 10/2003 | Shiu |
| 2003/0212449 A1 | 11/2003 | Cox |
| 2003/0233117 A1 | 12/2003 | Adams et al. |
| 2003/0236567 A1 | 12/2003 | Elliot |
| 2004/0015227 A1 | 1/2004 | Vardi et al. |
| 2004/0015229 A1 | 1/2004 | Fulkerson et al. |
| 2004/0098091 A1 | 5/2004 | Erbel et al. |
| 2004/0106972 A1 | 6/2004 | Deaton |
| 2004/0106978 A1 | 6/2004 | Greenberg et al. |
| 2004/0117003 A1 | 6/2004 | Ouriel et al. |
| 2004/0133266 A1 | 7/2004 | Clerc et al. |
| 2004/0138735 A1 | 7/2004 | Shaolian et al. |
| 2004/0162606 A1 | 8/2004 | Thompson |
| 2004/0171978 A1 | 9/2004 | Shalaby |
| 2004/0176832 A1 | 9/2004 | Hartley et al. |
| 2004/0181149 A1 | 9/2004 | Langlotz et al. |
| 2004/0215319 A1 | 10/2004 | Berra et al. |
| 2004/0215327 A1 | 10/2004 | Doig et al. |
| 2004/0215332 A1 | 10/2004 | Frid |
| 2004/0260383 A1 | 12/2004 | Stelter et al. |
| 2005/0010246 A1 | 1/2005 | Streeter et al. |
| 2005/0033406 A1 | 2/2005 | Barnhart et al. |
| 2005/0049678 A1 | 3/2005 | Cocks et al. |
| 2005/0065545 A1 | 3/2005 | Wallace |
| 2005/0070995 A1* | 3/2005 | Zilla et al. ................. 623/1.32 |
| 2005/0085900 A1 | 4/2005 | Case et al. |
| 2005/0102018 A1 | 5/2005 | Carpenter et al. |
| 2005/0102021 A1 | 5/2005 | Osborne |
| 2005/0131517 A1 | 6/2005 | Hartley et al. |
| 2005/0137682 A1 | 6/2005 | Justino |
| 2005/0143802 A1 | 6/2005 | Soykan et al. |
| 2005/0149166 A1 | 7/2005 | Schaeffer et al. |
| 2005/0154448 A1 | 7/2005 | Cully et al. |
| 2005/0159803 A1 | 7/2005 | Lad et al. |
| 2005/0165480 A1 | 7/2005 | Jordan et al. |
| 2005/0171598 A1 | 8/2005 | Schaeffer |
| 2005/0171599 A1 | 8/2005 | White |
| 2005/0177132 A1 | 8/2005 | Lentz et al. |
| 2005/0203606 A1 | 9/2005 | VanCamp |
| 2005/0216018 A1 | 9/2005 | Sennett |
| 2005/0222649 A1 | 10/2005 | Capuano et al. |
| 2005/0222667 A1 | 10/2005 | Hunt |
| 2005/0222668 A1 | 10/2005 | Schaeffer et al. |
| 2005/0222669 A1 | 10/2005 | Purdy |
| 2005/0228480 A1 | 10/2005 | Douglas et al. |
| 2005/0234542 A1 | 10/2005 | Melsheimer |
| 2005/0266042 A1 | 12/2005 | Tseng |
| 2005/0273155 A1 | 12/2005 | Bahler et al. |
| 2005/0283188 A1 | 12/2005 | Loshakove et al. |
| 2006/0015170 A1 | 1/2006 | Jones et al. |
| 2006/0030921 A1 | 2/2006 | Chu |
| 2006/0052799 A1 | 3/2006 | Middleman et al. |
| 2006/0069426 A1 | 3/2006 | Weinberger |
| 2006/0095104 A1 | 5/2006 | Magers et al. |
| 2006/0095114 A1 | 5/2006 | Hartley et al. |
| 2006/0100684 A1 | 5/2006 | Elliott |
| 2006/0106406 A1 | 5/2006 | Weinberger |
| 2006/0116748 A1 | 6/2006 | Kaplan et al. |
| 2006/0149360 A1 | 7/2006 | Schwammenthal et al. |
| 2006/0155358 A1 | 7/2006 | LaDuca et al. |
| 2006/0155359 A1 | 7/2006 | Watson |
| 2006/0155366 A1 | 7/2006 | LaDuca et al. |
| 2006/0167476 A1 | 7/2006 | Burdulis et al. |
| 2006/0173530 A1 | 8/2006 | Das |
| 2006/0190070 A1 | 8/2006 | Dieck et al. |
| 2006/0193892 A1 | 8/2006 | Furst et al. |
| 2006/0229709 A1 | 10/2006 | Morris et al. |
| 2006/0241740 A1 | 10/2006 | Vardi et al. |
| 2006/0271166 A1 | 11/2006 | Thill et al. |
| 2006/0276882 A1 | 12/2006 | Case et al. |
| 2006/0281966 A1 | 12/2006 | Peacock, III |
| 2007/0016281 A1 | 1/2007 | Melsheimer |
| 2007/0021822 A1 | 1/2007 | Boatman |
| 2007/0043425 A1 | 2/2007 | Hartley et al. |
| 2007/0050011 A1 | 3/2007 | Klein et al. |
| 2007/0055326 A1 | 3/2007 | Farley et al. |
| 2007/0055350 A1 | 3/2007 | Erickson et al. |
| 2007/0055358 A1 | 3/2007 | Krolik et al. |
| 2007/0055360 A1 | 3/2007 | Hanson et al. |
| 2007/0060989 A1 | 3/2007 | Deem et al. |
| 2007/0061002 A1 | 3/2007 | Paul, Jr. et al. |
| 2007/0067014 A1 | 3/2007 | Ke et al. |
| 2007/0073373 A1 | 3/2007 | Bonsignore |
| 2007/0088425 A1 | 4/2007 | Schaeffer |
| 2007/0112344 A1 | 5/2007 | Keilman |
| 2007/0135677 A1 | 6/2007 | Miller et al. |
| 2007/0142896 A1 | 6/2007 | Anderson et al. |
| 2007/0150051 A1 | 6/2007 | Arnault de la Menardiere et al. |
| 2007/0156167 A1 | 7/2007 | Connors et al. |
| 2007/0162104 A1 | 7/2007 | Frid |
| 2007/0167898 A1 | 7/2007 | Peters et al. |
| 2007/0167955 A1 | 7/2007 | Arnault de la Menardiere et al. |
| 2007/0168013 A1 | 7/2007 | Douglas |
| 2007/0168018 A1 | 7/2007 | Amplatz et al. |
| 2007/0179598 A1 | 8/2007 | Duerig |
| 2007/0185565 A1 | 8/2007 | Schwammenthal et al. |
| 2007/0207186 A1 | 9/2007 | Scanlon et al. |
| 2007/0208410 A1 | 9/2007 | Berra et al. |
| 2007/0213805 A1 | 9/2007 | Schaeffer et al. |
| 2007/0213807 A1 | 9/2007 | Roubin et al. |
| 2007/0219610 A1 | 9/2007 | Israel |
| 2007/0219627 A1 | 9/2007 | Chu et al. |
| 2007/0225797 A1 | 9/2007 | Krivoruhko |
| 2007/0233229 A1 | 10/2007 | Berra et al. |
| 2007/0237973 A1 | 10/2007 | Purdy et al. |
| 2007/0239256 A1 | 10/2007 | Weber et al. |
| 2007/0244542 A1 | 10/2007 | Greenan et al. |
| 2007/0244543 A1 | 10/2007 | Mitchell |
| 2007/0244547 A1 | 10/2007 | Greenan |
| 2007/0250154 A1 | 10/2007 | Greenberg et al. |
| 2007/0255388 A1 | 11/2007 | Rudakov et al. |
| 2008/0033527 A1 | 2/2008 | Nunez et al. |
| 2008/0064957 A1 | 3/2008 | Spence |
| 2008/0109058 A1 | 5/2008 | Greenberg et al. |
| 2008/0109066 A1 | 5/2008 | Quinn |
| 2008/0114444 A1 | 5/2008 | Yu |
| 2008/0114445 A1 | 5/2008 | Melsheimer et al. |
| 2008/0147173 A1 | 6/2008 | Mciff et al. |
| 2008/0167704 A1 | 7/2008 | Wright et al. |
| 2008/0176271 A1 | 7/2008 | Silver et al. |
| 2008/0195190 A1 | 8/2008 | Bland et al. |
| 2008/0195191 A1 | 8/2008 | Luo et al. |
| 2008/0215134 A1 | 9/2008 | Lawrence-Brown |
| 2008/0249598 A1 | 10/2008 | Sherry |
| 2008/0262595 A1 | 10/2008 | Chu et al. |
| 2008/0262598 A1 | 10/2008 | Elmaleh |
| 2008/0269789 A1 | 10/2008 | Eli |

(56) References Cited

U.S. PATENT DOCUMENTS

| | | |
|---|---|---|
| 2008/0275540 A1 | 11/2008 | Wen |
| 2008/0275542 A1 | 11/2008 | LaDuca et al. |
| 2008/0288044 A1 | 11/2008 | Osborne |
| 2008/0294234 A1 | 11/2008 | Hartley et al. |
| 2008/0300665 A1 | 12/2008 | Lootz et al. |
| 2008/0319528 A1 | 12/2008 | Yribarren et al. |
| 2009/0012597 A1 | 1/2009 | Doig et al. |
| 2009/0012602 A1 | 1/2009 | Quadri |
| 2009/0030497 A1 | 1/2009 | Metcalf et al. |
| 2009/0030502 A1 | 1/2009 | Sun et al. |
| 2009/0048663 A1 | 2/2009 | Greenberg |
| 2009/0054967 A1 | 2/2009 | Das |
| 2009/0062899 A1 | 3/2009 | Dang et al. |
| 2009/0069881 A1 | 3/2009 | Chalekian et al. |
| 2009/0069882 A1 | 3/2009 | Venturelli et al. |
| 2009/0082841 A1 | 3/2009 | Zacharias et al. |
| 2009/0082847 A1 | 3/2009 | Zacharias et al. |
| 2009/0099648 A1 | 4/2009 | Yu |
| 2009/0099649 A1 | 4/2009 | Chobotov et al. |
| 2009/0099650 A1 | 4/2009 | Bolduc et al. |
| 2009/0105809 A1 | 4/2009 | Lee et al. |
| 2009/0112233 A1 | 4/2009 | Xiao |
| 2009/0125096 A1 | 5/2009 | Chu et al. |
| 2009/0138067 A1 | 5/2009 | Pinchuk et al. |
| 2009/0149877 A1 | 6/2009 | Hanson et al. |
| 2009/0157014 A1 | 6/2009 | Osborne et al. |
| 2009/0164001 A1 | 6/2009 | Biggs et al. |
| 2009/0171437 A1 | 7/2009 | Brocker et al. |
| 2009/0192587 A1 | 7/2009 | Frid |
| 2009/0227997 A1 | 9/2009 | Wang et al. |
| 2009/0240316 A1 | 9/2009 | Bruszewski |
| 2009/0248134 A1 | 10/2009 | Dierking et al. |
| 2009/0254170 A1 | 10/2009 | Hartley et al. |
| 2009/0259290 A1 | 10/2009 | Bruszewski et al. |
| 2009/0287145 A1 | 11/2009 | Cragg et al. |
| 2010/0004728 A1 | 1/2010 | Rao et al. |
| 2010/0029608 A1 | 2/2010 | Finley et al. |
| 2010/0057186 A1 | 3/2010 | West et al. |
| 2010/0063575 A1 | 3/2010 | Shalev et al. |
| 2010/0070019 A1 | 3/2010 | Shalev |
| 2010/0082091 A1 | 4/2010 | Berez et al. |
| 2010/0161025 A1 | 6/2010 | Kuppurathanam et al. |
| 2010/0161026 A1 | 6/2010 | Brocker et al. |
| 2010/0211159 A1 | 8/2010 | Schmid et al. |
| 2010/0249899 A1 | 9/2010 | Chuter et al. |
| 2010/0256725 A1 | 10/2010 | Rasmussen |
| 2010/0274187 A1 | 10/2010 | Argentine |
| 2010/0274345 A1 | 10/2010 | Rust |
| 2010/0292774 A1 | 11/2010 | Shalev |
| 2010/0318171 A1 | 12/2010 | Porter et al. |
| 2011/0022149 A1 | 1/2011 | Cox et al. |
| 2011/0022153 A1* | 1/2011 | Schreck ............ A61F 2/07 623/1.13 |
| 2011/0093002 A1 | 4/2011 | Rucker et al. |
| 2011/0125251 A1 | 5/2011 | Cottone et al. |
| 2011/0152998 A1 | 6/2011 | Berez et al. |
| 2011/0208289 A1 | 8/2011 | Shalev |
| 2011/0208296 A1 | 8/2011 | Duffy et al. |
| 2011/0208297 A1 | 8/2011 | Tuval et al. |
| 2011/0208298 A1 | 8/2011 | Tuval et al. |
| 2011/0218607 A1 | 9/2011 | Arbefeuille et al. |
| 2011/0218609 A1* | 9/2011 | Chobotov ............ A61F 2/06 623/1.11 |
| 2011/0257720 A1 | 10/2011 | Peterson et al. |
| 2011/0257725 A1 | 10/2011 | Argentine et al. |
| 2011/0262684 A1 | 10/2011 | Wintsch et al. |
| 2011/0264184 A1 | 10/2011 | Heltai |
| 2011/0288622 A1 | 11/2011 | Chan et al. |
| 2011/0301702 A1 | 12/2011 | Rust et al. |
| 2011/0319983 A1 | 12/2011 | Zhu et al. |
| 2012/0143317 A1 | 6/2012 | Cam et al. |
| 2012/0150274 A1 | 6/2012 | Shalev et al. |
| 2012/0158038 A1 | 6/2012 | Leschinsky |
| 2012/0172929 A1 | 7/2012 | Shalev |
| 2012/0179236 A1 | 7/2012 | Benary et al. |
| 2012/0185031 A1 | 7/2012 | Ryan et al. |
| 2012/0271401 A1 | 10/2012 | Bruszewski et al. |
| 2012/0310324 A1 | 12/2012 | Benary et al. |
| 2012/0316634 A1 | 12/2012 | Shalev et al. |
| 2012/0323305 A1 | 12/2012 | Benary et al. |
| 2012/0330399 A1 | 12/2012 | Shalev et al. |
| 2013/0013050 A1 | 1/2013 | Shalev et al. |
| 2013/0013051 A1 | 1/2013 | Benary |
| 2013/0035751 A1 | 2/2013 | Shalev |
| 2013/0090722 A1 | 4/2013 | Shalev et al. |
| 2013/0131783 A1 | 5/2013 | Shalev et al. |
| 2013/0204343 A1 | 8/2013 | Shalev |
| 2013/0261994 A1 | 10/2013 | Raz et al. |
| 2013/0274866 A1 | 10/2013 | Cox et al. |
| 2013/0289587 A1 | 10/2013 | Shalev |
| 2013/0297005 A1 | 11/2013 | Shalev |
| 2014/0052236 A1 | 2/2014 | Shalev |
| 2014/0172072 A1 | 6/2014 | Shalev |
| 2014/0288635 A1 | 9/2014 | Shalev |
| 2014/0324154 A1 | 10/2014 | Shalev |
| 2014/0364930 A1 | 12/2014 | Strauss et al. |

FOREIGN PATENT DOCUMENTS

| | | |
|---|---|---|
| CN | 2817770 | 9/2006 |
| CN | 201058061 | 5/2008 |
| EP | 1177780 | 2/2002 |
| EP | 1325716 | 7/2003 |
| EP | 1470797 | 10/2004 |
| EP | 1759666 | 3/2007 |
| EP | 1961401 | 8/2008 |
| EP | 2266509 | 12/2010 |
| EP | 2298248 | 3/2011 |
| JP | 2002253682 | 9/2002 |
| WO | 98/06355 A1 | 2/1998 |
| WO | 99/34748 A1 | 7/1999 |
| WO | 00/28923 A1 | 5/2000 |
| WO | 02083038 | 10/2002 |
| WO | 03099108 | 12/2003 |
| WO | 2004017868 | 3/2004 |
| WO | 2005002466 | 1/2005 |
| WO | 2005/034809 A1 | 4/2005 |
| WO | 2005037138 | 4/2005 |
| WO | 2005041781 | 5/2005 |
| WO | 2005041783 | 5/2005 |
| WO | 2005046524 | 5/2005 |
| WO | 2006007389 | 1/2006 |
| WO | 2006028925 | 3/2006 |
| WO | 2006070372 | 7/2006 |
| WO | 2007022495 | 2/2007 |
| WO | 2007039587 | 4/2007 |
| WO | 2007084547 | 7/2007 |
| WO | 2007144782 | 12/2007 |
| WO | 2008008291 | 1/2008 |
| WO | 2008035337 | 3/2008 |
| WO | 2008042266 | 4/2008 |
| WO | 2008047092 | 4/2008 |
| WO | 2008047354 | 4/2008 |
| WO | 2008053469 | 5/2008 |
| WO | 2008066923 | 6/2008 |
| WO | 2008107885 | 9/2008 |
| WO | 2008140796 | 11/2008 |
| WO | 2009078010 | 6/2009 |
| WO | 2009116041 | 9/2009 |
| WO | 2009116042 | 9/2009 |
| WO | 2009118733 | 10/2009 |
| WO | 2010024869 | 3/2010 |
| WO | 2010024879 | 3/2010 |
| WO | 2010031060 | 3/2010 |
| WO | 2010045238 | 4/2010 |
| WO | 2010062355 | 6/2010 |
| WO | 2010088776 | 8/2010 |
| WO | 2010128162 | 11/2010 |
| WO | 2010150208 | 12/2010 |
| WO | 2011004374 | 1/2011 |
| WO | 2011007354 | 1/2011 |
| WO | 2011055364 | 5/2011 |
| WO | 2011064782 | 6/2011 |
| WO | 2011067764 | 6/2011 |

(56) References Cited

FOREIGN PATENT DOCUMENTS

| | | |
|---|---|---|
| WO | 2011070576 | 6/2011 |
| WO | 2011080738 | 7/2011 |
| WO | 2011095979 | 8/2011 |
| WO | 2011106532 | 9/2011 |
| WO | 2011106533 | 9/2011 |
| WO | 2011106544 | 9/2011 |
| WO | 2012049679 | 4/2012 |
| WO | 2012104842 | 8/2012 |
| WO | 2012111006 | 8/2012 |
| WO | 2012117395 | 9/2012 |
| WO | 2012176187 | 12/2012 |
| WO | 2013005207 | 1/2013 |
| WO | 2013030818 | 3/2013 |
| WO | 2013030819 | 3/2013 |
| WO | 2013065040 | 5/2013 |
| WO | 2013084235 | 6/2013 |
| WO | 2013171730 | 11/2013 |
| WO | 2014020609 | 2/2014 |
| WO | 2014108895 | 7/2014 |
| WO | 2014141232 | 9/2014 |
| WO | 2014188412 | 11/2014 |

OTHER PUBLICATIONS

Invitation to Pay Additional Fees dated Aug. 27, 2014 from the International Searching Authority in counterpart International Application No. PCT/IL14/50434.
Communication dated Nov. 26, 2014 from the U.S. Patent and Trademark Office in counterpart U.S. Appl. No. 13/383,128.
Communication dated Jan. 16, 2015 from the State Intellectual Property Office of the P.R.C. in counterpart application No. 201080062714.5.
Communication dated Feb. 3, 2015 from the U.S. Patent and Trademark Office in counterpart U.S. Appl. No. 12/447,684.
Communication dated Feb. 26, 2015 from the European Patent Office in counterpart application No. 12806964.8.
Communication dated Mar. 20, 2015 from the European Patent Office in counterpart application No. 08861980.4.
Communication dated Apr. 22, 2015 from the European Patent Office in counterpart application No. 12828495.7.
Communication dated May 15, 2015 from the U.S. Patent and Trademark Office in counterpart U.S. Appl. No. 13/577,161.
International Search Report and Written Opinion dated Jul. 30, 2014 from the International Searching Authority in counterpart International Application No. PCT/IL14/50174.
A non-final Office Action dated Feb. 28, 2014 in U.S. Appl. No. 13/512,778.
An International Preliminary Report on Patentability dated Jan. 7, 2014, which issued during the prosecution of Applicant's PCT/IL2012/000269.
An International Preliminary Report on Patentability dated Jan. 4, 2012, which issued during the prosecution of Applicant's PCT/IB2010/052861.
An International Preliminary Report on Patentability dated Dec. 23, 2013, which issued during the prosecution of Applicant's PCT/IL2012/000241.
An International Preliminary Report on Patentability dated Aug. 6, 2013, which issued during the prosecution of Applicant's PCT/IL2012/000060.
An English translation of an Office Action dated Oct. 8, 2014, which issued during the prosecution of Chinese Patent Application No. 201080036970.7.
An English translation of an Office Action dated Nov. 28, 2013, which issued during the prosecution of Chinese Patent Application No. 200880126889.0.
An English translation of an Office Action dated Jan. 28, 2014, which issued during the prosecution of Chinese Patent Application No. 201080036970.7.
An English translation of an Office Action dated May 16, 2014, which issued during the prosecution of Chinese Patent Application No. 200880126889.0.
An English translation of an Office Action dated Aug. 25, 2011, which issued during the prosecution of Chinese Patent Application No. 200880014919.9.
An English translation of an Office Action dated Feb. 16, 2013, which issued during the prosecution of Chinese Patent Application No. 200880126889.0.
An International Preliminary Report on Patentability dated Jan. 10, 2012, which issued during the prosecution of Applicant's PCT/IL2010/000549.
An International Preliminary Report on Patentability dated Jan. 17, 2012, which issued during the prosecution of Applicant's PCT/IL2010/000564.
A Notice of Allowance dated Aug. 2, 2012, which issued during the prosecution of U.S. Appl. No. 12/529,936.
An Advisory Action dated Feb. 13, 2014, which issued during the prosecution of Applicant's U.S. Appl. No. 13/807,880.
An International Preliminary Report on Patentability dated Jun. 5, 2012, which issued during the prosecution of Applicant's PCT/IL2010/000999.
An International Preliminary Report on Patentability dated Jun. 5, 2012, which issued during the prosecution of Applicant's PCT/IL2010/001018.
An International Preliminary Report on Patentability dated Jun. 10, 2014, which issued during the prosecution of Applicant's PCT/IL2012/050506.
A Notice of Allowance issued in U.S. Appl. No. 13/807,906 dated Oct. 10, 2014.
A Restriction Requirement dated Jan. 29, 2014, which issued during the prosecution of U.S. Appl. No. 13/519,971.
An International Preliminary Report on Patentability dated Jun. 12, 2012, which issued during the prosecution of Applicant's PCT/IL2010/001037.
An International Preliminary Report on Patentability dated Mar. 4, 2014, which issued during the prosecution of Applicant's PCT/IL2012/000300.
An International Preliminary Report on Patentability dated May 6, 2014, which issued during the prosecution of Applicant's PCT/IL2012/050424.
An International Preliminary Report on Patentability dated May 8, 2012, which issued during the prosecution of Applicant's PCT/IL2010/000917.
An International Preliminary Report on Patentability dated Nov. 18, 2014, which issued during the prosecution of Applicant's PCT/IL2012/000190.
An International Search Report and a Written Opinion both dated Apr. 18, 2011, which issued during the prosecution of Applicant's PCT/IL2010/001037.
An International Search Report and a Written Opinion both dated Aug. 4, 2011, which issued during the prosecution of Applicant's PCT/IL2010/000999.
An International Search Report and a Written Opinion both dated Aug. 31, 2012, which issued during the prosecution of Applicant's PCT/IL2012/000148.
An International Search Report and a Written Opinion both dated Dec. 3, 2010, which issued during the prosecution of Applicant's PCT/IL2010/000564.
An International Search Report and a Written Opinion both dated Feb. 4, 2011, which issued during the prosecution of Applicant's PCT/IB2010/052861.
An International Search Report and a Written Opinion both dated Jul. 13, 2012, which issued during the prosecution of Applicant's PCT/IL2012/000083.
An International Search Report and a Written Opinion both dated Jul. 17, 2012, which issued during the prosecution of Applicant's PCT/IL2012/000095.
An International Search Report and a Written Opinion both dated Jun. 14, 2013, which issued during the prosecution of Applicant's PCT/IL2012/050506.

(56) References Cited

OTHER PUBLICATIONS

An International Search Report and a Written Opinion both dated Jun. 28, 2011, which issued during the prosecution of Applicant's PCT/IL2011/000135.
An International Search Report and a Written Opinion both dated Jun. 30, 2009, which issued during the prosecution of Applicant's PCT/IL2008/001621.
An International Search Report and a Written Opinion both dated Mar. 10, 2011, which issued during the prosecution of Applicant's PCT/IL2010/000917.
An International Search Report and a Written Opinion both dated Mar. 11, 2009, which issued during the prosecution of Applicant's PCT/IL2007/001312.
An International Search Report and a Written Opinion both dated Mar. 15, 2013, which issued during the prosecution of Applicant's PCT/IL2012/050424.
An International Preliminary Report on Patentability dated Sep. 3, 2013, which issued during the prosecution of Applicant's PCT/IL2012/000095.
An International Search Report and a Written Opinion both dated Mar. 30, 2011, which issued during the prosecution of Applicant's PCT/IL2010/001018.
An International Search Report and a Written Opinion both dated May 23, 2011, which issued during the prosecution of Applicant's PCT/IL2010/001087.
An International Search Report and a Written Opinion both dated Nov. 5, 2010, which issued during the prosecution of Applicant's PCT/IL2010/000549.
An International Search Report and a Written Opinion both dated Nov. 27, 2012, which issued during the prosecution of Applicant's PCT/IL2012/000300.
An International Search Report and a Written Opinion both dated Oct. 1, 2012, which issued during the prosecution of Applicant's PCT/IL2012/000241.
An International Search Report and a Written Opinion both dated Oct. 4, 2012, which issued during the prosecution of Applicant's PCT/IL2012/000269.
An International Search Report and a Written Opinion both dated Sep. 6, 2012, which issued during the prosecution of Applicant's PCT/IL2012/000190.
An International Search Report and a Written Opinion both dated Apr. 28, 2014, which issued during the prosecution of Applicant's PCT/IL2014/050019.
An International Search Report dated Jul. 30, 2014, which issued during the prosecution of Applicant's PCT/IL2014/050174.
An International Search Report and a Written Opinion both dated Sep. 24, 2012, which issued during the prosecution of Applicant's PCT/IL2012/000060.
An International Search Report and a Written Opinion both dated Sep. 29, 2008, which issued during the prosecution of Applicant's PCT/IL2008/000287.
Notice of allowance dated Jun. 24, 2014, which issued during the prosecution of Applicant's U.S. Appl. No. 13/380,278.
An International Search Report dated Nov. 28, 2014, which issued during the prosecution of Applicant's PCT/IL2014/050434.
An Interview Summary dated Feb. 28, 2012, which issued during the prosecution of U.S. Appl. No. 12/529,936.
An Office Action dated Apr. 10, 2014, which issued during the prosecution of Applicant's U.S. Appl. No. 13/807,906.
An Office Action dated Apr. 24, 2014, which issued during the prosecution of Applicant's U.S. Appl. No. 13/380,278.
An Office Action dated Dec. 2, 2013, which issued during the prosecution of U.S. Appl. No. 13/807,880.
An office Action dated Feb. 25, 2013, which issued during the prosecution of U.S. Appl. No. 13/031,871.
An Office Action dated Feb. 27, 2013, which issued during the prosecution of U.S. Appl. No. 12/808,037.
An Office Action dated Jul. 24, 2014, which issued during the prosecution of Canadian Patent Application No. 2768228.
An Office Action dated Jul. 28, 2014, which issued during the prosecution of U.S. Appl. No. 13/031,871.
An Office Action dated Jun. 19, 2012, which issued during the prosecution of U.S. Appl. No. 12/808,037.
An Office Action dated Mar. 24, 2011, which issued during the prosecution of U.S. Appl. No. 12/529,936.
An Office Action dated Mar. 28, 2014, which issued during the prosecution of Applicant's U.S. Appl. No. 13/519,971.
An Office Action dated Apr. 27, 2011, which issued during the prosecution of U.S. Appl. No. 12/447,684.
An Office Action dated Apr. 28, 2014, which issued during the prosecution of Applicant's U.S. Appl. No. 13/939,798.
An Office Action dated May 20, 2013, which issued during the prosecution of U.S. Appl. No. 13/807,880.
An Office Action dated Nov. 12, 2010, which issued during the prosecution of U.S. Appl. No. 12/447,684.
An Office Action dated Nov. 3, 2014, which issued during the prosecution of Canadian Patent Application No. 2767596.
An Office Action dated Nov. 19, 2013, which issued during the prosecution of U.S. Appl. No. 13/663,117.
An Office Action dated Oct. 11, 2012, which issued during the prosecution of U.S. Appl. No. 13/031,871.
U.S. Appl. No. 61/219,758, filed Jun. 23, 2009.
U.S. Appl. No. 61/221,074, filed Jun. 28, 2009.
U.S. Appl. No. 61/496,613, filed Jun. 14, 2011.
An Office Action dated Oct. 28, 2011, which issued during the prosecution of U.S. Appl. No. 12/529,936.
U.S. Appl. No. 61/505,132, filed Jul. 7, 2011.
U.S. Appl. No. 61/678,182, filed Aug. 1, 2012.
U.S. Appl. No. 61/529,931, filed Sep. 1, 2011.
U.S. Appl. No. 61/553,209, filed Oct. 30, 2011.
U.S. Appl. No. 61/499,195, filed Jun. 21, 2011.
U.S. Appl. No. 61/749,965, filed Jan. 8, 2013.
Notice of Allowance dated Jun. 18, 2013, which issued during the prosecution of U.S. Appl. No. 13/523,296.
Office Action issued on Oct. 27, 2014 in Canadian Patent Application No. 2,785,953.
Ryhanen J., in "Biocompatibility evaluation of nickel-titanium shape memory metal alloy," Academic Dissertation, Faculty of Medicine, Department of Surgery, University of Oulu, Finland (May 1999).
Supplementary European Search Report dated Dec. 13, 2012, which issued during the prosecution of Applicant's European App No. 08719912.1.
Supplementary European Search Report dated Feb. 17, 2014, which issued during the prosecution of Applicant's European App No. 12803376.8.
Supplementary European Search Report dated Jun. 23, 2014, which issued during the prosecution of Applicant's European App No. 12741804.4.
An International Search Report and Written Opinion both dated Nov. 26, 2013, which issued during the prosecution of Applicant's PCT/IL2013/050656.
"E-vita® open plus" product brochure (JOTEC GmbH, Hechingen, Germany), 2010.
An Office action dated Sep. 4, 2014, from the U.S. Patent and Trademark Office in counterpart U.S. Appl. No. 13/519,971.
European Office Action dated Dec. 17, 2014 in European Patent Application No. 12803376.8.
An Office action dated Feb. 5, 2015, from the U.S. Patent and Trademark Office in counterpart U.S. Appl. No. 13/384,075.
European Search Report dated Feb. 24, 2014 in European Patent Application No. 12803376.8.
Fattori et al., Degenerative aneurysm of the descending aorta. Endovascular Treatment. pp. 1-11, 2007, European Association for Cardio-Thoracic Surgery.
International Preliminary Report on Patentability dated Jan. 12, 2010 in corresponding International Application No. PCT/IL2008/000287.
Fonseca A et al., "Intravascular ultrasound assessment of the novel AngioSculpt scoring balloon catheter for the treatment of complex coronary lesions," J Invasive Cardiol 20(1):21-7 (Jan. 2008).

(56) References Cited

OTHER PUBLICATIONS

Van Prehn J et al., "Oversizing of aortic stent grafts for abdominal aneurysm repair: a systematic review of the benefits and risks," Eur J Vase Endovase Surg. Jul. 2009:38(I):42-53. Epub May 9, 2009 (abstract only).
Invitation to Pay Additional Fees dated May 13, 2014, which issued during the prosecution of Applicant's PCT/IL2014/050019.
Invitation to Pay Additional Fees dated May 8, 2014, which issued during the prosecution of Applicant's PCT/IL2014/50174.
Khlif H et al., "Contribution to the Improvement of Textile Vascular Prostheses Crimping," Trends in Applied Sciences Research 6(9):1019-1027 (2011).
U.S. Appl. No. 61/775,964, filed Mar. 11, 2013.
U.S. Appl. No. 61/826,544, filed May 23, 2013.
U.S. Appl. No. 61/906,014, filed Nov. 19, 2013.
U.S. Appl. No. 61/926,533, filed Jan. 13, 2014.
U.S. Appl. No. 61/528,242, filed Aug. 28, 2011.
An English translation of an Office Action dated Mar. 19, 2015, which issued during the prosecution of Chinese Patent Application No. 201080036970.7.
A Notice of Allowance dated Jan. 20, 2015, which issued during the prosecution of U.S. Appl. No. 13/383,128.
A Notice of Allowance dated Nov. 7, 2014, which issued during the prosecution of U.S. Appl. No. 13/512,778.
An Office Action dated Aug. 15, 2014, which issued during the prosecution of U.S. Appl. No. 13/512,778.
An International Search Report and a Written Opinion both dated Mar. 18, 2015, which issued during the prosecution of Applicant's PCT/IL2014/050973.
An Office Action dated Apr. 14, 2015, which issued during the prosecution of U.S. Appl. No. 14/130,213.
An International Preliminary Report on Patentability dated Feb. 3, 2015, which issued during the prosecution of Applicant's PCT/IL2013/050656.
A Notice of Allowance dated Jan. 7, 2014, which issued during the prosecution of U.S. Appl. No. 13/663,117.
An Office Action dated Mar. 26, 2015, which issued during the prosecution of U.S. Appl. No. 13/514,240.
Communication dated Aug. 12, 2015 from the U.S. Patent and Trademark Office in counterpart U.S. Appl. No. 13/513,397.
Communication dated Sep. 23, 2015 from the U.S. Patent and Trademark Office in counterpart U.S. Appl. No. 13/384,075.
Communication dated Oct. 2, 2015 from the U.S. Patent and Trademark Office in counterpart U.S. Appl. No. 13/577,161.
Communication dated Oct. 27, 2015 from the European Patent Office in counterpart application No. 10835608.0.

* cited by examiner

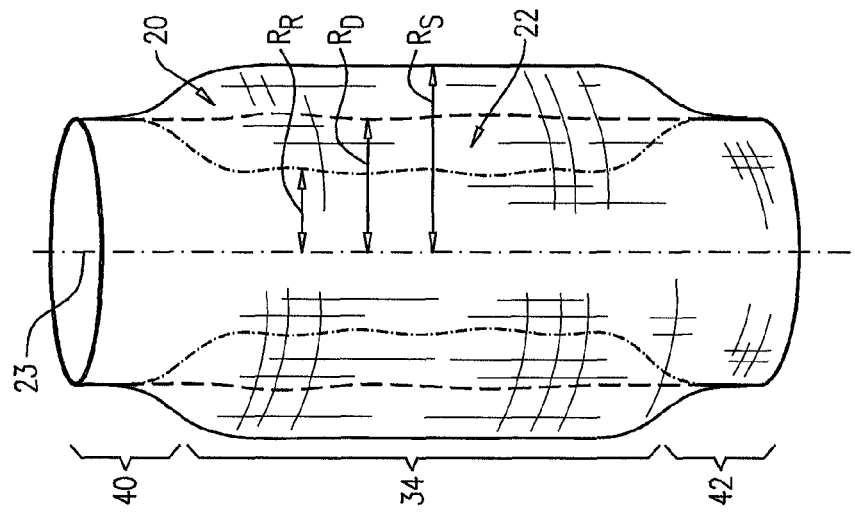
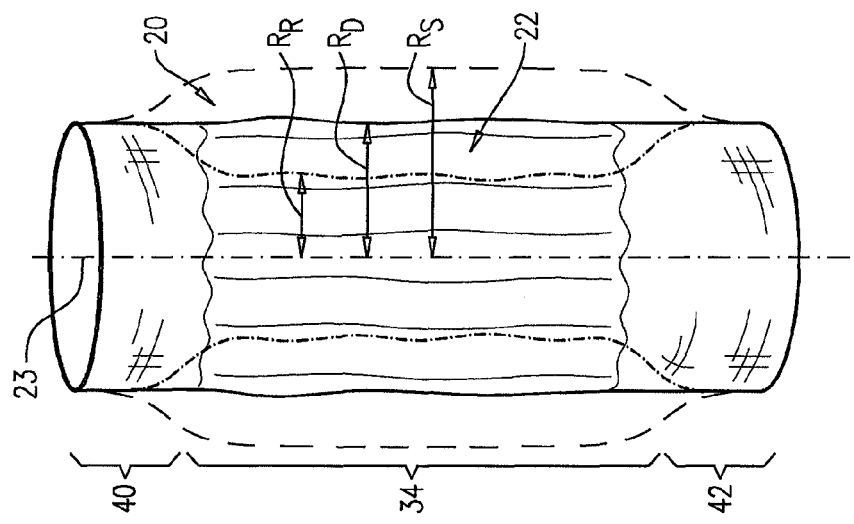
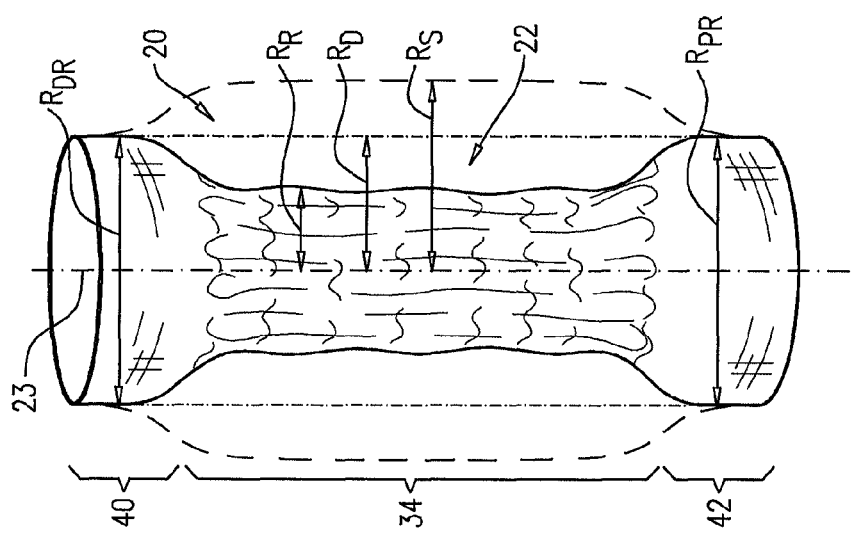

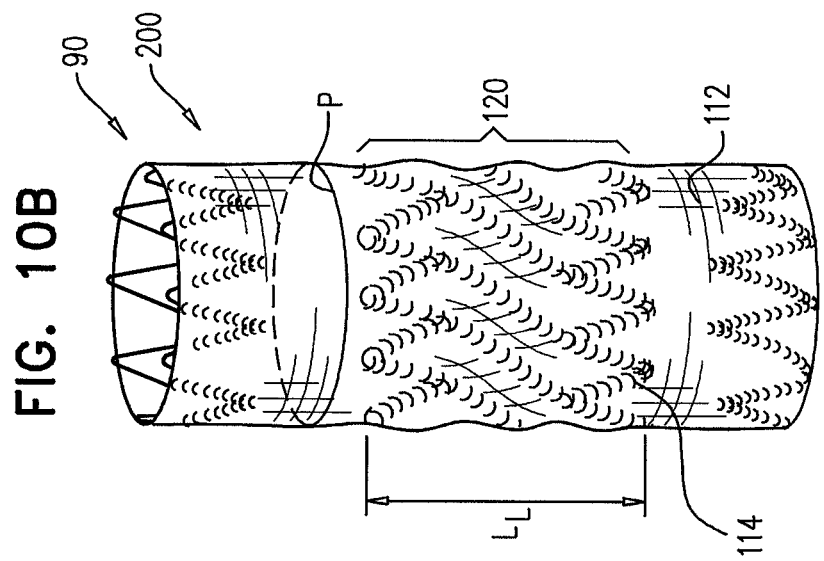
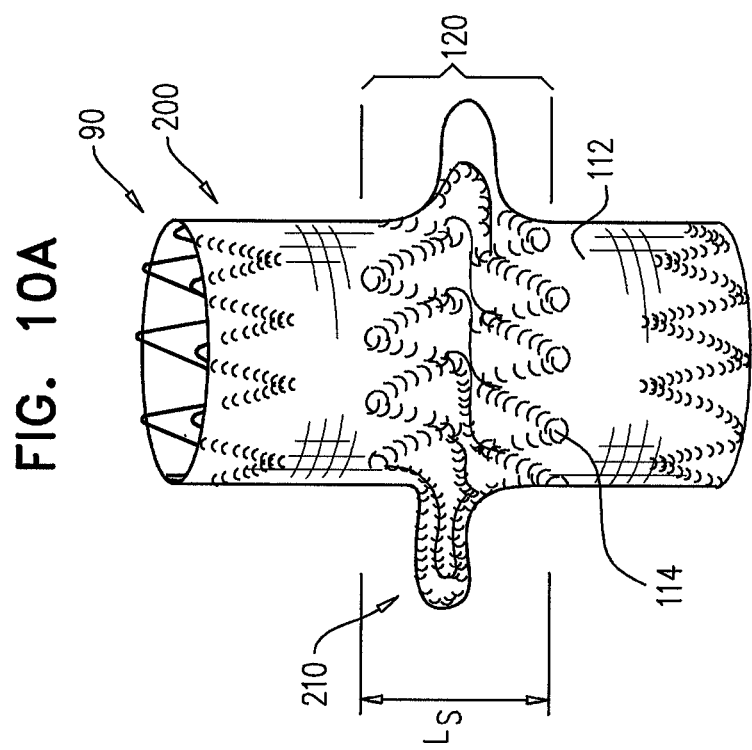

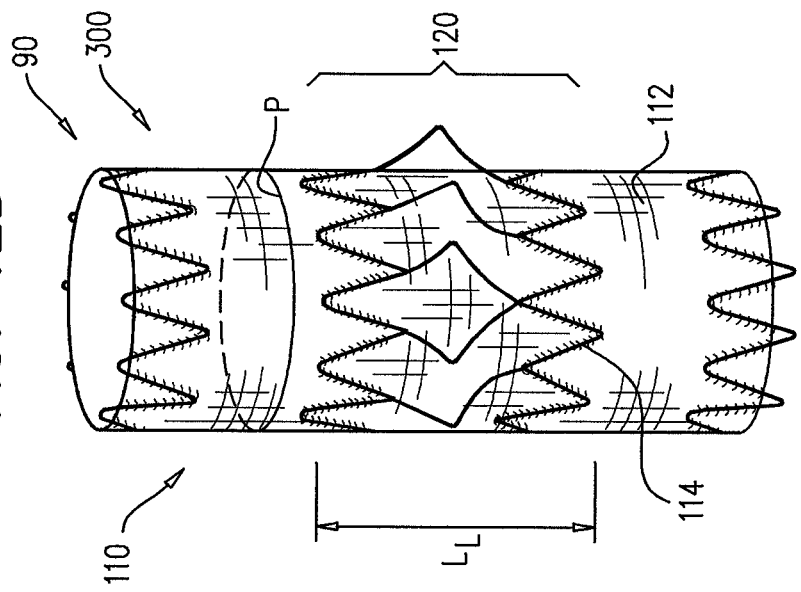
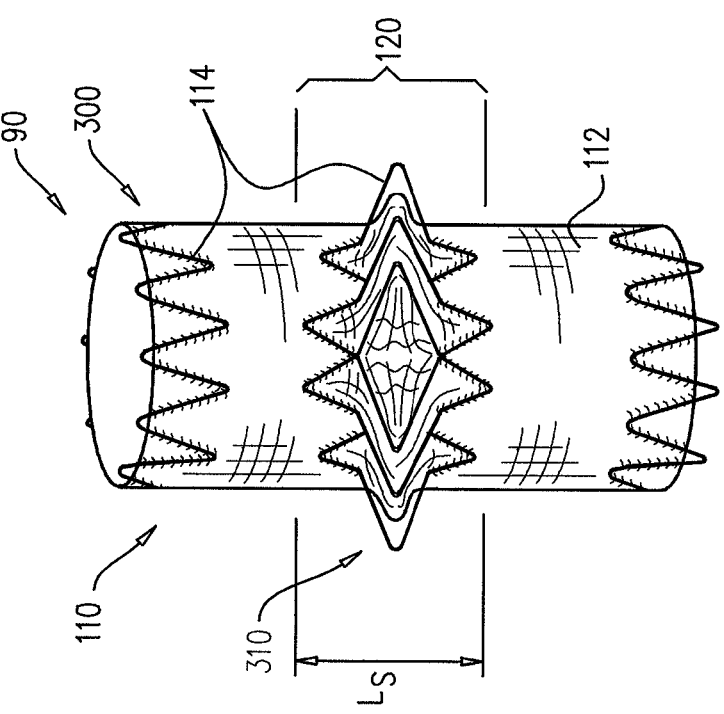

STENT-GRAFTS WITH POST-DEPLOYMENT VARIABLE RADIAL DISPLACEMENT

CROSS-REFERENCE TO RELATED APPLICATIONS

The present application is the US national stage of International Application PCT/IL2012/000148, filed Apr. 4, 2012, which claims priority from US Provisional Application 61/528,242, filed Aug. 28, 2011, and U.S. Provisional Application 61/553,209, filed Oct. 30, 2011, both of which are assigned to the assignee of the present application and are incorporated herein by reference.

FIELD OF THE APPLICATION

This present application relates generally to prostheses and surgical methods, and specifically to tubular prostheses, including endovascular stent-grafts, and surgical techniques for using the prostheses to maintain patency of body passages such as blood vessels, and treating aneurysms.

BACKGROUND OF THE APPLICATION

Endovascular prostheses are sometimes used to treat aortic aneurysms. Such treatment includes implanting a stent or stent-graft within the diseased vessel to bypass the anomaly. An aneurysm is a sac formed by the dilation of the wall of the artery. Aneurysms may be congenital, but are usually caused by disease or, occasionally, by trauma. Aortic aneurysms include abdominal aortic aneurysms ("i"), which form between the renal arteries and the iliac arteries, and thoracic aortic aneurysms ("TAAs"), which may occur in one or more of the descending aorta, the ascending aorta, and the aortic arch.

SUMMARY OF APPLICATIONS

Some applications of the present invention provide endovascular stent-grafts characterized by high physiological compliance. Such high physiological compliance minimizes the effect of the stent-grafts on the pulse profile of a blood vessel in which the stent-grafts are implanted, such as the aorta. Large-caliber arteries, in particular the aorta, provide the majority of arterial vascular compliance. The aorta and the branching large blood vessels thus act as a mechanical capacitor that expands during systole and contracts during diastole. Conventional endovascular stent-grafts often comprise substantially non-compliant graft materials, and even when such stent-grafts utilize relatively flexible medical fabrics, the stent-grafts are usually essentially fully expanded under diastolic arterial pressure. As a result, conventional stent-grafts substantially do not radially pulsate with the systolic cycle. Therefore, implantation of conventional stent-grafts results in the replacement of a large portion of a compliant aorta with a non- or low-compliant prosthesis. Conventional endovascular stent-grafts thus generally change the aortic pulse profile. Such a reduction in the overall vascular compliance may have deleterious cardiovascular effects, by increasing the load of the heart and/or decreasing the effectiveness of propagation of the systolic pulse from the heart into the smaller-caliber vasculature.

Some applications of the present invention provide endovascular stent-grafts that have beneficial effects on the peripheral vascular load, while using well-proven, gold-standard, medical-grade textiles and metallic alloys. The stent-grafts are configured to provide mechanical compliance that maintains (or, in some cases, even restores) the native, healthy, physiological compliance of the arterial segment in which the stent-grafts are implanted.

In some applications of the present invention, an endovascular stent-graft comprises a generally tubular body, which is configured to assume a radially-compressed delivery state and a radially-expanded deployment state. The body comprises a flexible stent member and a tubular fluid flow guide. The tubular flow guide comprises a graft material, which is generally non- or minimally-elastic. The body includes a compliance-restoration body portion that extends axially along a portion of the body. When the body is in the radially-expanded deployment state, the compliance-restoration body portion is (a) characterized by a greatest diastolic outer radius when the body is internally pressurized by fluid having a pressure of 80 mmHg, typically by blood during diastole in an adult human, and (b) radially expandable to a greatest systolic outer radius when the body is internally pressurized by fluid having a pressure of 120 mmHg, typically by blood during systole in an adult human. The greatest systolic outer radius is typically at least 5% greater than the greatest diastolic outer radius, such as at least 10%, e.g., 15%, greater than greatest diastolic outer radius. This increase in outer radius at greater internal pressure occurs because the stent is heat-set to have a diameter that is substantially (e.g., 5%-20%) less than the graft's fully-expanded (i.e., without folds) diameter, and the stent has the appropriate radial compliance such that the entire stent-graft substantially changes its radius between a state in which the stent-graft is internally pressurized by a nominal hydrostatic diastolic pressure and a state in which the stent-graft is internally pressurized by a nominal hydrostatic systolic pressure.

For example, the stent member may comprise a highly elastic (e.g. flexible stainless steel) or a superelastic (e.g. Nitinol) alloy that is heat-set to have a first relaxed outer diameter, e.g., 23 mm, along the compliance-restoration body portion when the body is not internally pressurized by fluid. The tubular flow guide is configured to have a greater, second outer diameter, e.g., 30 mm, when internally pressurized to systolic pressure, e.g., 120 mmHg. When pressurized by fluid having a diastolic pressure, e.g., 80 mmHg, the compliance-restoration body portion assumes a diastolic outer diameter that is slightly larger than the first relaxed outer diameter, e.g., between 26 and 27 mm. When pressurized by the fluid having systolic pressure, e.g., 120 mmHg, the compliance-restoration body portion assumes a systolic outer diameter equal to the second outer diameter, e.g., 30 mm, as limited by the diameter of the non-compliant graft material. For some applications, proximal and distal end-portions of the stent-graft have respective relaxed outer diameters that are greater than the first relaxed outer diameter, which may help provide good fixation and sealing with the blood vessel wall.

In contrast, conventional thoracic aortic stent-grafts often comprise a Nitinol stent skeleton having a heat-set diameter of 32 mm and a tubular woven PET graft cylinder having a diameter of 30 mm, sewn to the stent skeleton. Such conventional stent-grafts may have a relaxed diameter of 30 mm, and do not allow for further expansion during systole. Conventional stent-grafts thus do not provide the radial compliance provided by some applications of the present invention.

In some applications of the present invention, a variable-length endovascular stent-graft comprises a generally tubular body, which comprises a fluid flow guide and a plurality of structural stent elements attached to at least a portion of the fluid flow guide. The body includes a variable-length section that extends axially along a portion of body. The body, including the variable-length section, is configured to assume a radially-compressed delivery state and a radially-expanded deployment state. The variable-length section, while radially-expanded in the deployment state, is configured to enable a change in an axial length thereof of at least 5 mm.

This change in axial length enables the stent-graft to accommodate any elongation of the blood vessel between the ends of the stent-graft that may occur after implantation of the stent-graft. Such elongation often occurs after implantation of a stent-graft. Because the stent-graft excludes the aneurysm from the blood circulation, the aneurysm thromboses, decomposes and shrinks, causing the blood vessel to become longer and narrower. Typically, such elongation occurs over a long period of time, and the stent-graft provides long-term accommodation of the elongation. Such accommodation decreases the risk of the stent-graft becoming dislodged, and decreases the risk of endoleak. Alternatively or additionally, this change in axial length provides axial compliance for reducing vascular resistance, similar to the radial compliance described above.

When the body is in the radially-expanded deployment state, the variable-length section is configured to assume an axially-shortest state thereof, in which state typically one or more of the structural stent elements are arranged along the variable-length section such that the variable-length section has no structural-stent-element-free axial portions having axial lengths greater than 5% of a greatest outer diameter of the fluid flow guide along the variable-length section when in its axially-shortest state; for some applications, the variable-length section has no structural-stent-element-free portions when in its axially-shortest state. Typically, the variable-length section is configured such that the structural stent elements thereof do not undergo plastic deformation as the axial-length changes.

Typically, the body is configured such that elasticity of graft material of the fluid flow guide provides less than 5% of a change in an axial length of the variable-length section. In other words, the change in the axial length of the variable-length section is not primarily enabled by stretching of the graft material of the fluid flow guide.

There is therefore provided, in accordance with an application of the present invention, apparatus including an endovascular stent-graft, which includes a generally tubular body, which body (a) is configured to assume a radially-compressed delivery state and a radially-expanded deployment state, and (b) includes:

a flexible stent member; and a tubular fluid flow guide, which includes a graft material, and is attached to the stent member, wherein the body includes a compliance-restoration body portion, which extends axially along a portion of the body, and which includes a portion of the stent member and a portion of the fluid flow guide, wherein, when the body is in the radially-expanded deployment state, the compliance-restoration body portion is (a) characterized by a greatest diastolic outer radius when the body is internally pressurized by fluid having a pressure of 80 mmHg, and (b) radially expandable to a greatest systolic outer radius when the body is internally pressurized by fluid having a pressure of 120 mmHg, and wherein the greatest systolic outer radius is at least 5% greater than the greatest diastolic outer radius, such as at least 10% greater than the greatest diastolic outer radius.

For some applications, the fluid flow guide of the compliance-restoration body portion is shaped so as to be expandable to a maximum greatest outer radius equal to the greatest systolic outer radius of the compliance-restoration body portion, such that the compliance-restoration body portion is limited by the fluid flow guide from assuming an outer radius that is greater than the maximum greatest outer radius.

For some applications, the stent member is heat-set to cause the compliance-restoration body portion to assume the greatest diastolic outer radius when the body is internally pressurized by the fluid having the pressure of 80 mmHg.

For any of the applications described above, when the body is in the radially-expanded deployment state, the compliance-restoration body portion may be characterized by a greatest relaxed outer radius when the body is not internally pressurized by fluid, which greatest relaxed outer radius is no more than 95% of the greatest diastolic outer radius. For some applications, the stent member is heat-set to cause the compliance-restoration body portion to assume the greatest relaxed outer radius when unconstrained.

For any of the applications described above, the graft material may include a woven graft.

For any of the applications described above, the graft material of the portion of the fluid flow guide may be at least partially folded when the body is in the radially-expanded deployment state and is internally pressured by the fluid of having the pressure of 80 mmHg.

For any of the applications described above, the fluid flow guide, if not attached to the stent member, may be configured to assume first and second perimeters when internally pressurized by fluid having a pressure of 80 and 120 mmHg, respectively, the second perimeter being no more than 10% greater than the first perimeter.

For any of the applications described above, the fluid flow guide, if not attached to the stent member, may be configured to assume first and second perimeters when internally pressurized by fluid having a pressure of 80 and 120 mmHg, respectively, the second perimeter being between 0.5% and 5% greater than the first perimeter.

For any of the applications described above, the stent member may include a plurality of structural stent elements that are indirectly connected to one another by the fluid flow guide.

For any of the applications described above, the stent member may include a plurality of interconnected structural stent elements.

For any of the applications described above, the greatest systolic outer radius may be no more than 30% greater than the greatest diastolic outer radius.

For any of the applications described above, the greatest diastolic outer radius may be between 7.5 mm and 25 mm, when the body is in the radially-expanded deployment state.

For any of the applications described above, the greatest systolic outer radius may be between 8.5 mm and 30 mm, when the body is in the radially-expanded deployment state.

For any of the applications described above, the body may further includes distal and proximal portions, longitudinally between which the compliance-restoration body portion is disposed, when the body is in the radially-expanded deployment state, the distal and proximal portions may be (a) characterized by greatest diastolic distal- and proximal-end-portion radii, respectively, when the body is internally pressurized by fluid having a pressure of 80 mmHg, and (b) radially expandable to greatest systolic distal- and proximal-endportion radii, respectively, when the body is internally pressurized by fluid having a pressure of 120 mmHg, the greatest systolic distal-end-portion outer radius may be less than 2% greater than the greatest diastolic distal-end-portion outer radius, and the greatest systolic proximal-end-portion outer radius may be less than 2% greater than the greatest diastolic proximal-end-portion outer radius.

For any of the applications described above, the body may further include distal and proximal portions, longitudinally between which the compliance-restoration body portion is disposed, and respective greatest radii of the distal and the proximal portions may be each at least 5% greater than a greatest relaxed outer radius of the compliance-restoration body portion, when the body is unconstrained in the radially-expanded deployment state.

For any of the applications described above, the body may further include distal and proximal portions, longitudinally between which the compliance-restoration body portion is disposed, and respective greatest radii of the distal and the proximal portions may be each at least 5% greater than the greatest diastolic outer radius, when the body is in the radially-expanded deployment state.

For any of the applications described above, the body may further include distal and proximal portions, longitudinally between which the compliance-restoration body portion is disposed, and a greatest outer radius of the distal portion, when unconstrained, may be between 2 and 10 mm greater than the greatest systolic outer radius, when the body is in the radially-expanded deployment state.

For any of the applications described above, the graft material may include a material selected from the group of materials consisting of: Polyethylene terephthalate (PET), Dacron, Polytetrafluoroethylene (PTFE), ePTFE, and a combination of two or more of these materials.

For any of the applications described above, the stent member may include a superelastic alloy.

For any of the applications described above, the stent-graft may be configured to self-expand from the delivery state to the deployment state.

For any of the applications described above:

the flexible stent member may include a plurality of structural stent elements attached to at least a portion of the fluid flow guide, the body may include a variable-length section, which extends axially along a portion of the body, and which includes one or more of the structural stent elements and a portion of the fluid flow guide, the body, including the variable-length section, may be configured to assume the radially-compressed delivery state and the radially-expanded deployment state, wherein, when the body is in the radially-expanded deployment state, the variable-length section may be configured to:

enable a change in an axial length thereof of at least 5 mm, and assume an axially-shortest state thereof, in which state the one or more of the structural stent elements are arranged along the variable-length section such that the variable-length section has no structural-stent-element-free axial portions having axial lengths greater than 5% of a greater outer diameter of the fluid flow guide along the variable-length section when in its axially-shortest state.

There is further provided, in accordance with an application of the present invention, apparatus including an endovascular stent-graft, which includes a generally tubular body, which body includes:

a fluid flow guide, which includes a graft material; and a plurality of structural stent elements attached to at least a portion of the fluid flow guide, wherein the body includes a variable-length section, which extends axially along a portion of the body, and which includes one or more of the structural stent elements and a portion of the fluid flow guide, wherein the body, including the variable-length section, is configured to assume a radially-compressed delivery state and a radially-expanded deployment state, wherein, when the body is in the radially-expanded deployment state, the variable-length section is configured to:

enable a change in an axial length thereof of at least 5 mm, and assume an axially-shortest state thereof, in which state the one or more of the structural stent elements are arranged along the variable-length section such that the variable-length section has no structural-stent-element-free axial portions having axial lengths greater than 5% of a greatest outer diameter of the fluid flow guide along the variable-length section when in its axially-shortest state.

For some applications, the one or more of the structural stent elements are arranged along the variable-length section such that the variable-length section has no structural-stent-element-free axial portions, when the variable-length section is in the axially-shortest state when the body is in the radially-expanded deployment state.

For some applications, the body is configured such that elasticity of the graft material provides less than 5% of the change in the axial length of the variable-length section.

For some applications, the variable-length section is configured such that the structural stent elements thereof do not undergo plastic deformation during the change in axial length.

For some applications, the variable-length section is configured such that the enabled change in the axial length is no more than 10% of a greatest outer diameter of the fluid flow guide along the variable-length section when the variable-length section is in the axially-shortest state.

For any of the applications described above, the variable-length section may be configured such that the enabled change in the axial length is equal to at least 10% of a greatest outer diameter of the fluid flow guide along the variable-length section when the variable-length section is in the axially-shortest state.

For any of the applications described above, a surface coverage ratio of the one or more of the structural stent elements of the variable-length section on the fluid flow guide may be equal to at least 5% when the variable-length section is in the axially-shortest state when the body is in the radially-expanded deployment state.

For any of the applications described above, when the body is in the radially-expanded deployment state, the variable-length section may be configured to undergo the change in the axial length in response to a change in fluid pressure within the fluid flow guide.

For any of the applications described above, when the body is in the radially-expanded deployment state, the variable-length section may be configured to undergo an increase in the axial length, and not a decrease in the axial length.

For any of the applications described above, when the body is in the radially-expanded deployment state, the variable-length section may be configured to cyclically undergo an increase in the axial length that alternates with a decrease in the axial length.

For any of the applications described above, the variable-length section may be configured to undergo (a) an increase in the axial length in response to an increase in fluid pressure within the fluid flow guide, and (b) a decrease in the axial length in response to a decrease in the fluid pressure within the fluid flow guide.

For any of the applications described above, the variable-length section may be configured to undergo (a) an increase in the axial length in response to a decrease in fluid pressure within the fluid flow guide, and (b) a decrease in the axial length in response to an increase in the fluid pressure within the fluid flow guide.

For any of the applications described above, the variable-length section may be configured such that during a 5 mm change in the axial length, an average wall thickness of the graft material changes by no more than 15%.

For any of the applications described above, the variable-length section may be configured to assume a folded position at least when the variable-length section is in the axially-shortest state, in which folded position a first longitudinal subsection of the fluid flow guide is radially sandwiched between second and third longitudinal subsections of the fluid flow guide.

For any of the applications described above, the variable-length section may be configured such that in the folded position the second longitudinal subsection radially surrounds the first longitudinal subsection, and at least one of the one or more of the structural stent elements of the variable-length section is attached to the second longitudinal subsection. For some applications, the variable-length section is configured such that in the folded position the first longitudinal subsection radially surrounds the third longitudinal subsection, and at least one of the one or more of the structural stent elements of the variable-length section is attached to the third longitudinal subsection. For some applications, the variable-length section is configured such that none of the structural stent elements of the body is attached to the first longitudinal subsection.

For any of the applications described above, the variable-length section may be shaped so as to define, at least when the variable-length section is in the axially-shortest state, a radially-outward bulge at least partially around a perimeter of an axial site on the variable-length section, which radially-outward bulge includes the one or more of the structural elements of the variable-length section. For some applications, the variable-length section is configured such that a radial dimension of the bulge decreases as the axial length of the variable-length section increases. For some applications, the variable-length section, when in an axially-longest state, is not shaped so as to define the bulge.

For any of the applications described above, the variable-length section may be shaped so as to define, at least when the variable-length section is in the axially-shortest state, a radially-inward indentation at least partially around a perimeter of an axial site on the variable-length section, which indentation includes the one or more of the structural elements of the variable-length section. For some applications, the variable-length section is configured such that a radial dimension of the indentation decreases as the axial length of the variable-length section increases. For some applications, the variable-length section, when in an axially-longest state, is not shaped so as to define the indentation.

For any of the applications described above, the variable-length section may be configured such that when the variable-length section undergoes the change in the axial length, a proximal end of the variable-length section rotates with respect to a distal end of the variable-length section.

For any of the applications described above, the variable-length section may be shaped so as to define, at least when the variable-length section is in the axially-shortest state, at least one single-sided helix, which includes the one or more of the structural elements. For some applications, the variable-length section is configured such that a step size of the at least one-single-sided helix increases as the axial length of the variable-length section increases.

For any of the applications described above, the variable-length section may be shaped so as to define, at least when the variable-length section is in the axially-shortest state, at least one right-handed helix and at least one left-handed helix, which helices include the one or more of the structural elements. For some applications, the variable-length section is configured such that respective step sizes of the right- and left-handed helices either both increase, or both decrease as axial length of the variable-length section increases.

For any of the applications described above:

the body may include a compliance-restoration body portion, which extends axially along a portion of the body, and which includes a portion of the structural stent elements and a portion of the fluid flow guide, when the body is in the radially-expanded deployment state, the compliance-restoration body portion may be (a) characterized by a greatest diastolic outer radius when the body is internally pressurized by fluid having a pressure of 80 mmHg, and (b) radially expandable to a greatest systolic outer radius when the body is internally pressurized by fluid having a pressure of 120 mmHg, and the greatest systolic outer radius may be at least 5% greater than the greatest diastolic outer radius.

There is still further provided, in accordance with an application of the present invention, a method including:

providing an endovascular stent-graft, which includes a generally tubular body, which includes a flexible stent member, and a tubular fluid flow guide, which includes a graft material, and is attached to the stent member, wherein the body includes a compliance-restoration body portion, which extends axially along a portion of the body, and which includes a portion of the stent member and a portion of the fluid flow guide;

transvascularly introducing the stent-graft into a blood vessel of a human subject while the body is in a radially-compressed delivery state; and thereafter, transitioning the body to a radially-expanded deployment state in the blood vessel, in which state the compliance-restoration body portion is characterized by (a) a greatest diastolic outer radius when the body is internally pressurized by blood of the subject during diastole, and (b) a greatest systolic outer radius when the body is internally pressurized by blood of the subject during systole, which greatest systolic outer radius is at least 5% greater than the greatest diastolic outer radius.

For some applications, transitioning the body to the deployment state includes allowing the body to self-expand.

For some applications, the greatest systolic outer radius is at least 10% greater than the greatest diastolic outer radius.

For some applications, providing the stent-graft includes providing the stent-graft in which the fluid flow guide of the compliance-restoration body portion is shaped so as to be expandable to a maximum greatest outer radius equal to the greatest systolic outer radius of the compliance-restoration body portion, such that the compliance-restoration body portion is limited by the fluid flow guide from assuming an outer radius that is greater than the maximum greatest outer radius.

For some applications, providing the stent-graft includes providing the stent-graft in which the fluid flow guide, if not attached to the stent member, is configured to assume first and second perimeters when internally pressurized by fluid having a pressure of 80 and 120 mmHg, respectively, the second perimeter being no more than 10% greater than the first perimeter.

For some applications:

the body further includes distal and proximal portions, longitudinally between which the compliance-restoration body portion is disposed, when the body is in the radially-expanded deployment state, the distal and proximal portions are characterized by (a) greatest diastolic distal- and proximal-end-portion radii, respectively, when the body is internally pressurized by the blood during diastole, and (b) greatest systolic distal- and proximal-end-portion radii, respectively, when the body is internally pressurized by the blood during systole, the greatest systolic distal-end-portion outer radius is less than 2% greater than the greatest diastolic distal-end-portion outer radius, and the greatest systolic proximal-end-portion outer radius is less than 2% greater than the greatest diastolic proximal-end-portion outer radius.

For some applications, the greatest systolic outer radius is no more than 30% greater than the greatest diastolic outer radius.

For some applications:

the flexible stent member includes a plurality of structural stent elements attached to at least a portion of the fluid flow guide, the body includes a variable-length section, which extends axially along a portion of the body, and which includes one or more of the structural stent elements and a portion of the fluid flow guide, the body, including the variable-length section, is configured to assume the radially-compressed delivery state and the radially-expanded deployment state, after the body is transitioned to the radially-expanded deployment state, the variable-length section is configured to enable a change in an axial length thereof of at least 5 mm, and if the variable-length section assumes an axially-shortest state thereof while the body is in the radially-expanded deployment state, the one or more of the structural stent elements are arranged along the variable-length section such that the variable-length section has no structural-stent-element-free axial portions having axial lengths greater than 5% of a greatest outer diameter of the fluid flow guide along the variable-length section when in its axially-shortest state.

There is additionally provided, in accordance with an application of the present invention, a method including:

providing an endovascular stent-graft, which includes a generally tubular body, which includes a fluid flow guide, which includes a graft material, and a plurality of structural stent elements attached to at least a portion of the fluid flow guide, wherein the body includes a variable-length section, which extends axially along a portion of the body, and which includes one or more of the structural stent elements and a portion of the fluid flow guide, transvascularly introducing the stent-graft into a blood vessel of a human subject while the body, including the variable-length section, is in a radially-compressed delivery state; and thereafter, transitioning the body to a radially-expanded deployment state in the blood vessel, in which state the variable-length section is configured to enable a change in an axial length thereof of at least 5 mm, wherein, if the variable-length section assumes an axially-shortest state thereof while the body is in the radially-expanded deployment state, the one or more of the structural stent elements are arranged along the variable-length section such that the variable-length section has no structural-stent-element-free axial portions having axial lengths greater than 5% of a greatest outer diameter of the fluid flow guide along the variable-length section when in its axially-shortest state.

For some applications, if the variable-length section assumes an axially-shortest state thereof while the body is in the radially-expanded deployment state, the one or more of the structural stent elements are arranged along the variable-length section such that the variable-length section has no structural-stent-element-free axial portions.

For some applications, providing the stent-graft includes providing the stent-graft in which the body is configured such that elasticity of the graft material provides less than 5% of the change in the axial length of the variable-length section.

For some applications, providing the stent-graft includes providing the stent-graft in which the variable-length section is configured such that the structural stent elements thereof do not undergo plastic deformation during the change in axial length.

For some applications, providing the stent-graft includes providing the stent-graft in which the variable-length section is configured such that the enabled change in the axial length is no more than 10% of a greatest outer diameter of the fluid flow guide along the variable-length section when the variable-length section is in the axially-shortest state.

For some applications, when the body is in the radially-expanded deployment state, the variable-length section is configured to undergo the change in the axial length in response to a change in fluid pressure within the fluid flow guide.

For some applications, when the body is in the radially-expanded deployment state, the variable-length section is configured to undergo an increase in the axial length, and not a decrease in the axial length.

For some applications, when the body is in the radially-expanded deployment state, the variable-length section is configured to cyclically undergo an increase in the axial length that alternates with a decrease in the axial length. For some applications, the variable-length section is configured to undergo (a) an increase in the axial length in response to an increase in fluid pressure within the fluid flow guide, and (b) a decrease in the axial length in response to a decrease in the fluid pressure within the fluid flow guide.

For some applications, the variable-length section is configured such that during a 5 mm change in the axial length, an average wall thickness of the graft material changes by no more than 15%.

For some applications, the variable-length section is configured to assume a folded position at least when the variable-length section is in the axially-shortest state, in which folded position a first longitudinal subsection of the fluid flow guide is radially sandwiched between second and third longitudinal subsections of the fluid flow guide.

For some applications, the variable-length section is shaped so as to define, at least when the variable-length section is in the axially-shortest state, a radially-outward bulge at least partially around a perimeter of an axial site on the variable-length section, which radially-outward bulge includes the one or more of the structural elements of the variable-length section.

For some applications, the variable-length section is shaped so as to define, at least when the variable-length section is in the axially-shortest state, a radially-inward indentation at least partially around a perimeter of an axial site on the variable-length section, which indentation includes the one or more of the structural elements of the variable-length section.

For some applications, the body includes a compliance-restoration body portion, which extends axially along a portion of the body, and which includes a portion of the structural stent elements and a portion of the fluid flow guide; and after the body is transitioned to the radially-expanded deployment state, the compliance-restoration body portion is characterized by (a) a greatest diastolic outer radius when the body is internally pressurized by blood flow of the subject during diastole, and (b) a greatest systolic outer radius when the body is internally pressurized by a blood of the subject during systole, which greatest systolic outer radius is at least 5% greater than the greatest diastolic outer radius.

The present invention will be more fully understood from the following detailed description of applications thereof, taken together with the drawings, in which:

BRIEF DESCRIPTION OF THE DRAWINGS

FIGS. 3A-C are schematic illustrations of yet another configuration of the endovascular stent-graft of FIGS. 1A and 1B, in accordance with an application of the present invention;

FIGS. 10A and 10B are schematic illustrations of the variable-length stent-graft of FIG. 9A in exemplary axially-shorter and axially-longer states, respectively, in accordance with an application of the present invention;

FIGS. 12A and 12B are schematic illustrations of the variable-length stent-graft of FIG. 11 in exemplary axially-shorter and axially-longer states, respectively, in accordance with an application of the present invention.

DETAILED DESCRIPTION OF APPLICATIONS

Figure 1A:
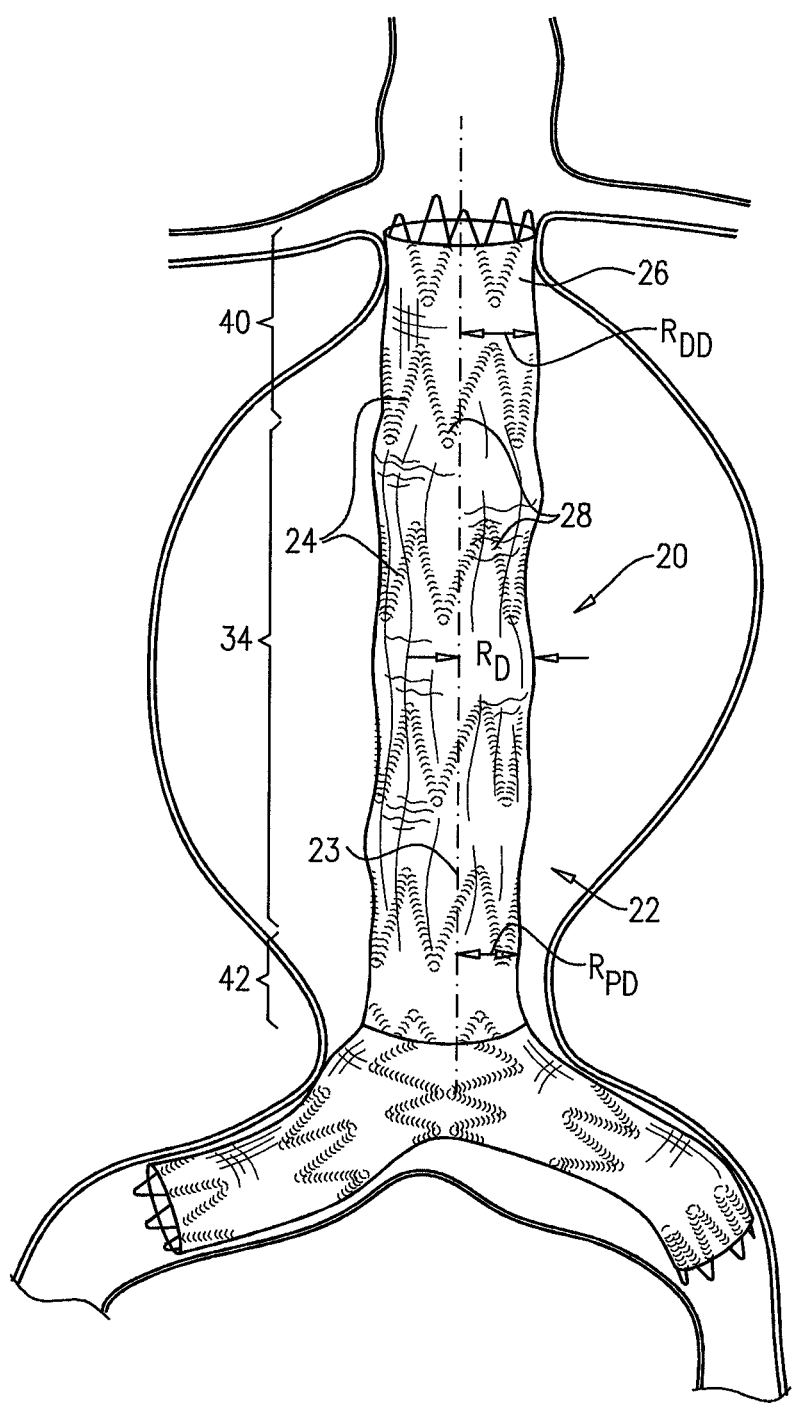
FIGS. 1A and 1B are schematic illustrations of an endovascular stent-graft, in accordance with an application of the present invention.
Figure 1B:
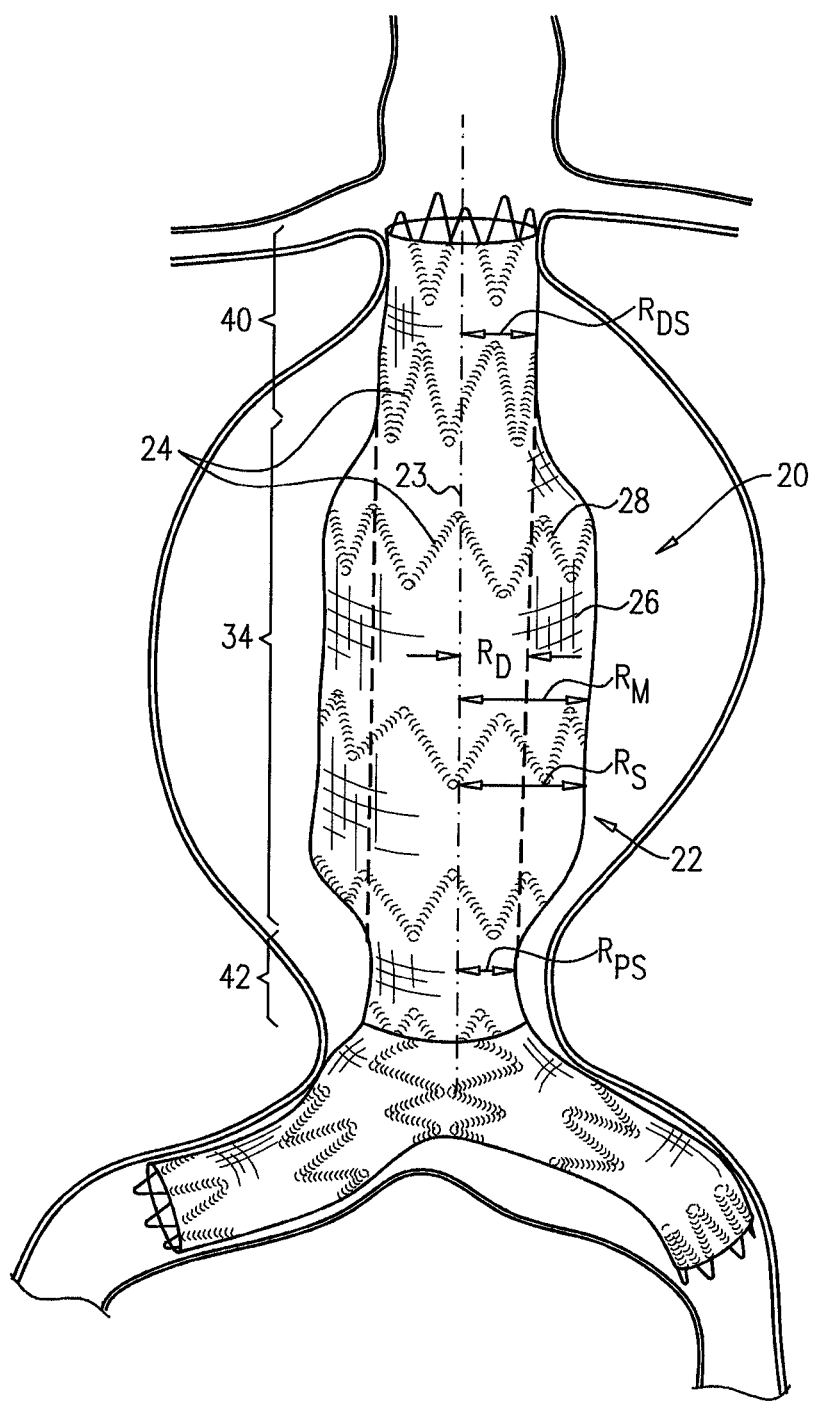

FIGS. 1A and 1B are schematic illustrations of an endovascular stent-graft 20, in accordance with an application of the present invention. Stent-graft 20 comprises a generally tubular body 22 having a central longitudinal axis 23. Body 22 is configured to assume (a) a radially-compressed delivery state, typically when the body is initially positioned in a delivery catheter, and (b) a radially-expanded deployment state, upon deployment from the delivery catheter. Both FIGS. 1A and 1B show the stent-graft with body 22 in its radially-expanded deployment state. Body 22 is shown during diastole of an adult human in FIG. 1A, and during systole of the adult human in FIG. 1B.

Body 22 comprises a flexible stent member 24, and a tubular fluid flow guide 26. The fluid flow guide is attached to the stent member, such as by suturing or stitching. The flexible stent member may be attached to an internal and/or an external surface of the fluid flow guide. Optionally, a portion of the structural stent elements may be attached (e.g., sutured) to the internal surface of the fluid flow guide, and another portion to the external surface of the fluid flow guide. Flexible stent member 24 comprises a plurality of structural stent elements 28, which are either indirectly connected to one another by the fluid flow guide (as shown), and/or interconnected with one another (configuration not shown). For some applications, structural stent elements 24 comprise a metal. Alternatively or additionally, the structural stent elements comprise a self-expanding material, such that body 22 (and, optionally, stent-graft 20) is self-expandable.

Alternatively or additionally, the structural stent elements comprise one or more metallic alloys, such as one or more superelastic metal alloys, a shape memory metallic alloy, and/or Nitinol.

Fluid flow guide 26 comprises a graft material, i.e., at least one biologically-compatible substantially blood-impervious flexible sheet. The flexible sheet may comprise, for example, a polyester, a polyethylene (e.g., a poly-ethylene-terephthalate), a polymeric film material (such as a fluoropolymer, e.g., polytetrafluoroethylene), a polymeric textile material (e.g., woven polyethylene terephthalate (PET)), natural tissue graft (e.g., saphenous vein or collagen), Polytetrafluoroethylene (PTFE), ePTFE, Dacron, or a combination of two or more of these materials. The graft material optionally is woven. The graft material of fluid flow guide 26 is generally non- or minimally-elastic.

Typically, stent-graft 20 is configured to self-expand from the delivery state to the deployment state. For example, stent member 24 may be heat-set to cause stent-graft 20 to self-expand from the delivery state to the deployment state.

Body 22 includes a compliance-restoration body portion 34, which extends axially along a portion of body 22, and which comprises a portion of stent member 24 and a portion of fluid flow guide 26. When body 22 is in the radially-expanded deployment state, as shown in FIGS. 1A and 1B, compliance-restoration body portion 34 is:
characterized by a greatest diastolic outer radius $R_D$ when body 22 is internally pressurized by fluid having a pressure of 80 mmHg, typically by blood during diastole in an adult human, as shown in FIG. 1A (and also by dashed lines in FIG. 1B); and
radially expandable to a greatest systolic outer radius $R_S$ when body 22 is internally pressurized by fluid having a pressure of 120 mmHg, typically by blood during systole in an adult human, as shown in FIG. 1B. For some applications, compliance-restoration body portion 34 expands to greatest systolic outer radius $R_S$ even when the body is internally pressured by fluid having a pressure of greater than 120 mmHg.

Greatest systolic outer radius $R_S$ is typically at least 5% greater than greatest diastolic outer radius $R_D$, such as at least 10% greater than greatest diastolic outer radius $R_D$, e.g., at least 15% greater than greatest diastolic outer radius $R_D$. Alternatively or additionally, greatest systolic outer radius $R_S$ is no more than 30% greater than the greatest diastolic outer radius $R_D$. This increase in outer radius at greater internal pressure occurs because the stent is heat-set to have a diameter that is substantially (e.g., 5%-20%) less than the graft's fully-expanded (i.e., without folds) diameter, and the stent has the appropriate radial compliance such that the entire stent-graft substantially changes its radius between a state in which the stent-graft is internally pressurized by a nominal hydrostatic diastolic pressure and a state in which the stent-graft is internally pressurized by a nominal hydrostatic systolic pressure.

For some applications, fluid flow guide 26 of compliance-restoration body portion 34 is shaped so as to be expandable to a maximum greatest outer radius $R_M$ equal to greatest systolic outer radius $R_S$ of compliance-restoration body portion 34, such that the compliance-restoration body portion is limited by the fluid flow guide from assuming an outer radius that is greater than the maximum greatest outer radius $R_M$. (The outer radius might not otherwise be limited by stent member 24, which is typically highly compliant and deformable, e.g., initially highly elastically deformable and subsequently, plastically deformable.) Typically, maximum greatest outer radius $R_M$ of fluid flow guide 26 is greater than the greatest diastolic outer radius of stent member 24, such as at least 5%, at least 10%, or at least 20% greater than greatest diastolic outer radius $R_D$ of stent member 24. During diastole, the inward compressive force applied by stent-member 24 is countered by the outward force applied by the internally pressurizing fluid (typically, diastolically-pressurized blood). These opposing forces jointly retain the fluid flow guide (and thus the entire compliance-restoration body portion 34) at greatest diastolic outer radius $R_D$.

For some applications, when body 22 is in the radially-expanded deployment state: (a) greatest diastolic outer radius $R_D$ is at least 7.5 mm, no more than 25 mm, and/or between 7.5 mm and 25 mm, and/or (b) greatest systolic outer radius $R_S$ is at least 8.5 mm, no more than 30 mm, and/or between 8.5 mm and 30 mm.

As mentioned above, the graft material of fluid flow guide 26 is generally non- or minimally-elastic. Therefore, when compliance-restoration body portion 34 is internally pressured by diastolic pressure, and is thus characterized greatest diastolic outer radius $R_D$ (which is less than maximum greatest outer radius $R_M$ of fluid flow guide 26), the graft material of the compliance-restoration portion is at least partially folded. In other words, during diastole, the outer radius of compliance-restoration body portion 34 is less than the maximum outer radius of the fluid flow guide (though the actual circumference of the fluid flow guide remains essentially the same, so the graft material of the fluid flow guide must assume small folds to accommodate this state). (The actual circumference is to be understood as measuring the actual length of the fabric's wall if the fabric were to be flattened to remove any folds, invaginations, or bulges caused by the radial contraction of the fluid flow guide.)

Fluid flow guide 26, if not attached to stent member 24 (e.g., before completion of manufacture of stent-graft 20), is configured to assume first and second perimeters when internally pressurized by fluid having a pressure of 80 and 120 mmHg, respectively. For some applications, the second perimeter is no more than 10% greater than the first perimeter, such as no more than 5% greater than the first perimeter. Alternatively or additionally, for some applications, the second perimeter is between 0.5% and 5% greater than the first perimeter.

For some applications, body 22 further includes distal and proximal portions 40 and 42, longitudinally between which compliance-restoration body portion 34 is disposed. When body 22 is in the radially-expanded deployment state, distal and proximal portions 40 and 42 are:
characterized by greatest diastolic distal- and proximal-end-portion radii $R_{DD}$ and $R_{PD}$, respectively, when body 22 is internally pressurized by fluid having a pressure of 80 mmHg, typically by blood during diastole in an adult human, as shown in FIG. 1A; and
radially expandable to greatest systolic distal- and proximal-end-portion radii $R_{DS}$ and $R_{PS}$, respectively, when body 22 is internally pressurized by fluid having a pressure of 120 mmHg, typically by blood during systole in an adult human, as shown in FIG. 1B.

For some applications, greatest systolic distal-end-portion outer radius $R_{DS}$ is less than 2% greater than greatest diastolic distal-end-portion outer radius $R_{DD}$, and/or greatest systolic proximal-end-portion outer radius $R_{PS}$ is less than 2% greater than greatest diastolic proximal-end-portion outer radius $R_{PD}$. In other words, the radii of distal and proximal portions 40 and 42 change only slightly, or not at all, during the transition between diastole and systole. (In contrast, the outer radius of compliance-restoration body portion 34 changes substantially (e.g., by at least 5%), during the transition between diastole and systole, as described above.)

Figure 2A:
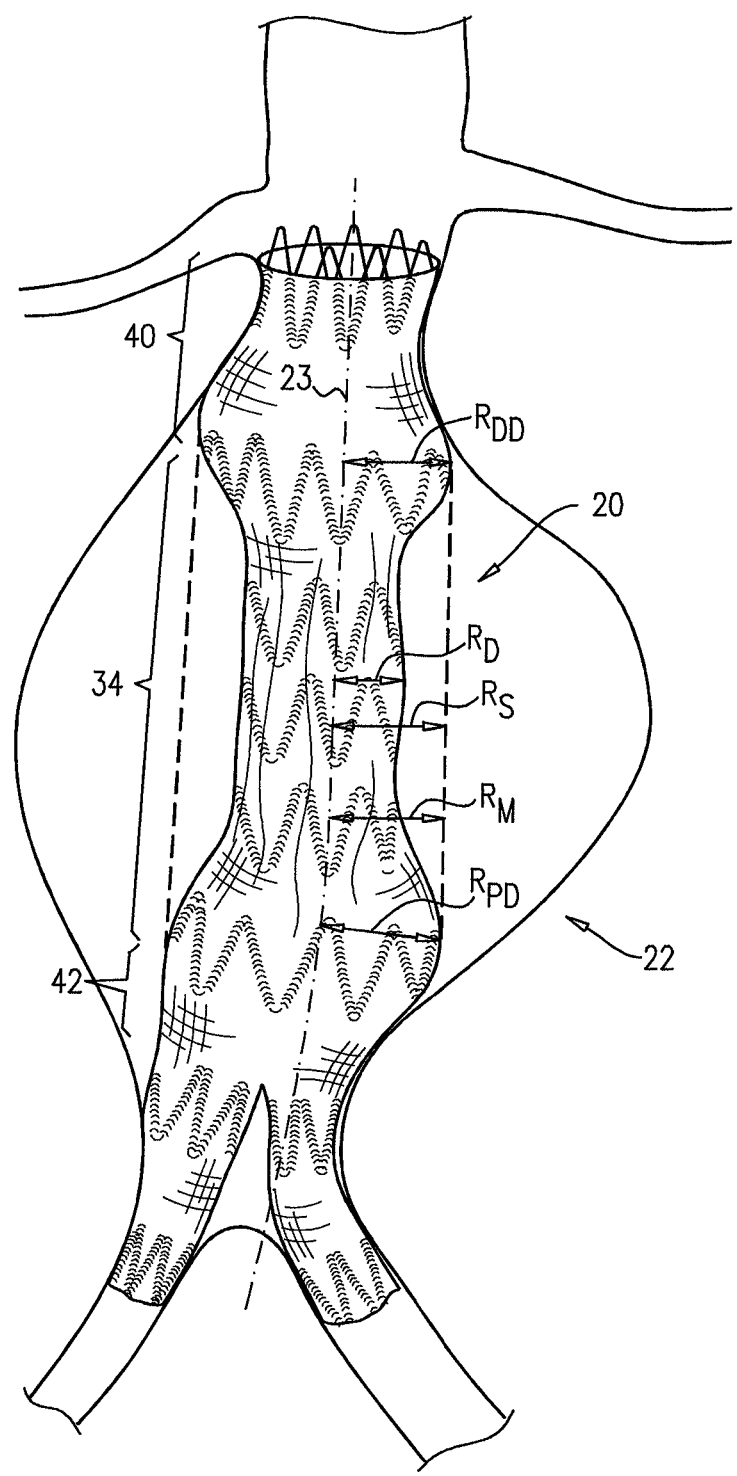
FIGS. 2A and 2B are schematic illustrations of another configuration of the endovascular stent-graft of FIGS. 1A and 1B, in accordance with an application of the present invention.
Figure 2B:
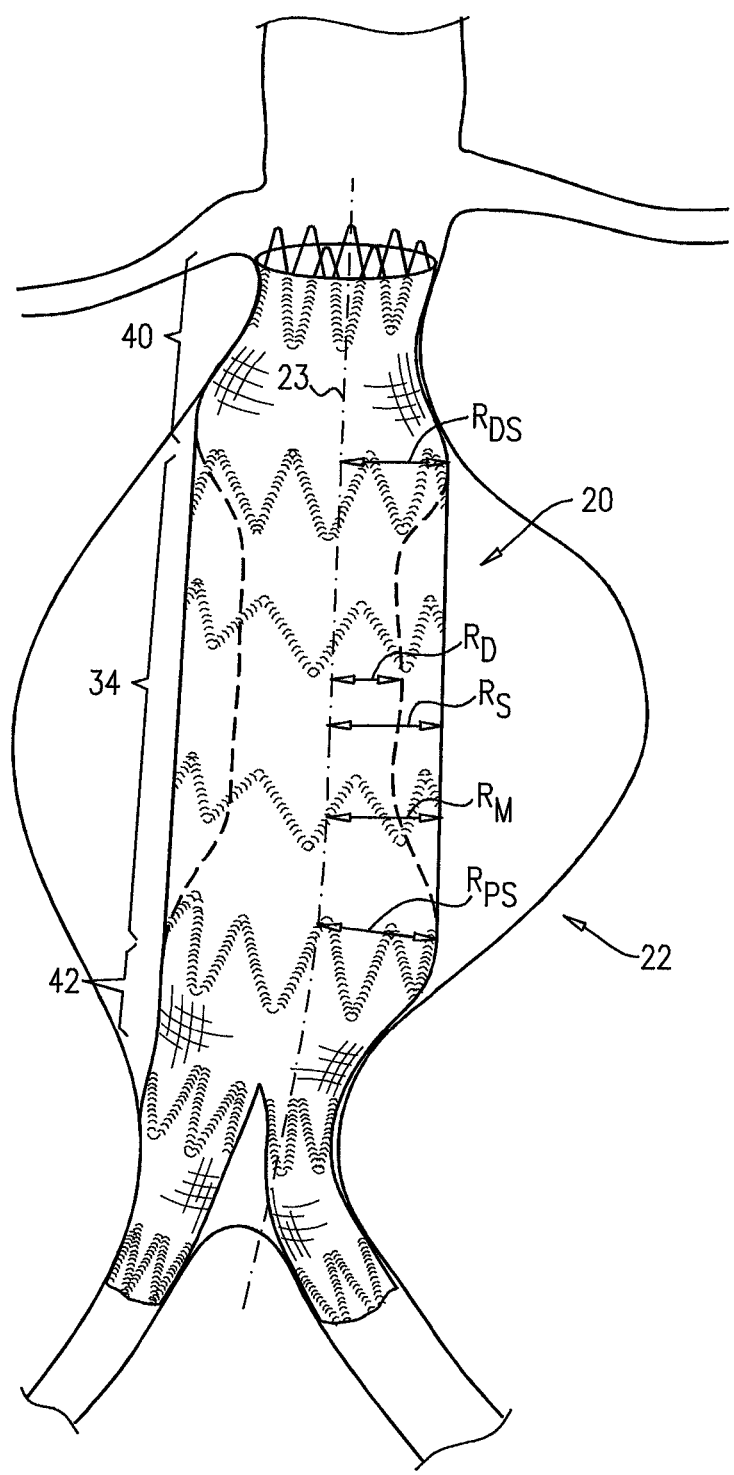

Reference is still made to FIGS. 1A and 1B, and is additionally made to FIGS. 2A and 2B, which are schematic illustrations of another configuration of endovascular stent-graft 20, in accordance with an application of the present invention. Both FIGS. 2A and 2B show the stent-graft with body 22 in its radially-expanded deployment state. Body 22 is shown during diastole of an adult human in FIG. 2A, and during systole of the adult human in FIG. 2B.

In a first configuration, as shown in FIGS. 1A and 1B, stent-graft 20 is configured such that:
greatest diastolic outer radius $R_D$ is approximately equal to (e.g., within +/−20% of) greatest diastolic distal-end-portion outer radius $R_{DD}$ and/or greatest diastolic proximal-end-portion outer radius $R_{PD}$; and
greatest systolic outer radius $R_S$ is greater than (e.g., at least 5% greater than, such as at least 15% greater than)

greatest systolic distal-end-portion outer radius $R_{DS}$ and/or greatest systolic proximal-end-portion outer radius $R_{PS}$.

In a second configuration, as shown in FIGS. 2A and 2B, stent-graft 20 is configured such that:

greatest diastolic distal-end-portion outer radius $R_{DD}$ is greater than (e.g., at least 5% greater than, such as at least 10% greater than) greatest diastolic outer radius $R_D$, and/or greatest diastolic proximal-end-portion outer radius $R_{PD}$ is greater than (e.g., at least 5% greater than, such as at least 10% greater than) greatest diastolic outer radius $R_D$, and greatest systolic outer radius $R_S$ is approximately equal to (e.g., within +/−20% of) greatest systolic distal-end-portion outer radius $R_{DS}$ and/or greatest systolic proximal-end-portion outer radius $R_{PS}$.

In a third configuration (not shown), stent-graft 20 is configured such that:

greatest diastolic outer radius $R_D$ is less than (e.g., at least 10% less than, such as at least 15% less than) greatest diastolic distal-end-portion outer radius $R_{DD}$ and/or greatest diastolic proximal-end-portion outer radius $R_{PD}$; and greatest systolic outer radius $R_S$ is greater than (e.g., at least 10% greater than, such as at least 15% greater than) greatest systolic distal-end-portion outer radius $R_{DS}$ and/or greatest systolic proximal-end-portion outer radius $R_{PS}$.

Reference is now made to FIGS. 3A-C, which are schematic illustrations of yet another configuration of endovascular stent-graft 20, in accordance with an application of the present invention. This configuration may be implemented in combination with any of the three configurations described immediately hereinabove with reference to FIGS. 1A-B and 2A-B. All of FIGS. 3A, 3B, and 3C show stent-graft 20 with body 22 in its radially-expanded deployment state. In this configuration, when body 22 is in its radially-expanded deployment state, compliance-restoration body portion 34, when not internally pressured by fluid, is characterized by a greatest relaxed outer radius $R_R$ that is less than greatest diastolic outer radius $R_D$ (and thus also less than even greater greatest systolic outer radius $R_S$). This greatest relaxed outer radius $R_R$ occurs only during manufacture and does not occur in vivo (except perhaps briefly during the implantation procedure), because upon deployment and radial expansion of body 22 to its radially-expanded deployment state, the body is internally subjected to at least diastolic blood pressure.

In FIG. 3A, body 22 is shown when it is not internally pressured by fluid. In this non-pressurized state, compliance-restoration body portion 34 is characterized by a greatest relaxed outer radius $R_R$ that is no more than 95% of greatest diastolic outer radius $R_D$, such as no more than 90% of greatest diastolic outer radius $R_D$. Typically, stent member 24 is heat-set to cause compliance-restoration body portion 34 to assume greatest relaxed outer radius $R_R$ when unconstrained, i.e., when no forces are applied to the compliance-restoration body portion by a delivery tool, walls of a blood vessel, or otherwise. As used in the present application, including in the claims, an "unconstrained" element is an element to which no forces are applied by a delivery tool, walls of a blood vessel, or otherwise.

In FIG. 3B, body 22 is shown internally pressurized by fluid having a pressure of 80 mmHg, typically by blood during diastole in an adult human. In this diastolically-pressurized state, compliance-restoration body portion 34 is characterized by greatest diastolic outer radius $R_D$. As described hereinabove with reference to FIGS. 1A-B, during diastole, the inward compressive force applied by stent-member 24 is countered by the outward force applied by the internally pressurizing fluid (typically, diastolically-pressurized blood). These opposing forces jointly retain the fluid flow guide (and thus the entire compliance-restoration body portion 34) at greatest diastolic outer radius $R_D$.

In FIG. 3C, body 22 is shown internally pressurized by fluid having a pressure of 120 mmHg, typically by blood during systole in an adult human. In this systolically-pressurized state, compliance-restoration body portion 34 is characterized by greatest diastolic outer radius $R_S$.

Reference is again made to FIG. 3A. For some applications, when body 22 is unconstrained in the radially-expanded deployment state, distal and proximal portions 40 and 42 are characterized by greatest relaxed distal- and proximal-end-portion radii $R_{DR}$ and $R_{PR}$, respectively, when body 22 is not internally pressurized by fluid. For some applications, when body 22 is in the radially-expanded deployment state, greatest relaxed distal-end-portion outer radius $R_{DR}$ is at least 5% greater than greatest relaxed outer radius $R_R$ of compliance-restoration body portion 34, and/or greatest relaxed proximal-end-portion outer radius $R_{PR}$ is at least 5% greater than greatest relaxed outer radius $R_R$. Such greater radii may help provide proper fixation to and sealing with the blood vessel wall.

Figure 4:
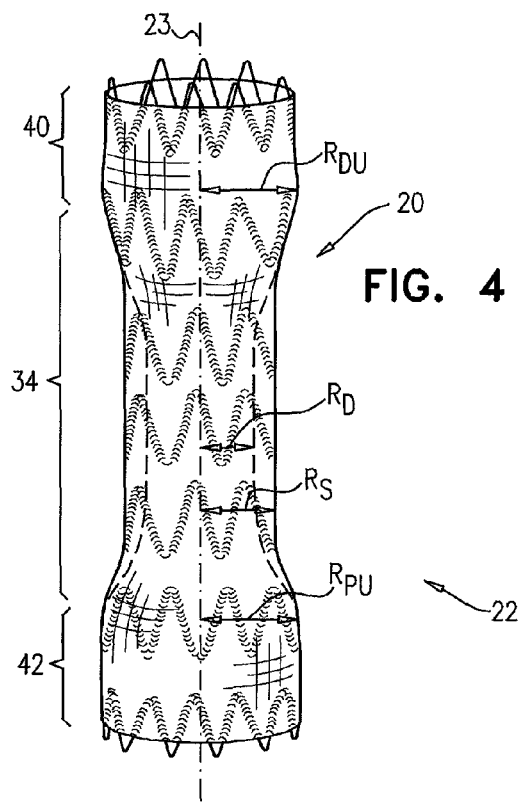
FIG. 4 is a schematic illustration of still another configuration of the endovascular stent-graft of FIGS. 1A and 1B, in accordance with an application of the present invention.

Reference is now made to FIG. 4, which is a schematic illustration of yet another configuration of endovascular stent-graft 20, in accordance with an application of the present invention. FIG. 4 shows the stent-graft with body 22 in its radially-expanded deployment state during systole, with distal and proximal portions 40 and 42 shown by way of illustration in a radially-expanded state while unconstrained, i.e., while no forces are applied to these portions by a delivery tool, walls of a blood vessel, or otherwise. The shape of compliance-restoration body portion 34 during diastole is also shown by dashed lines.

In this configuration, stent-graft 20 is configured such that:

a greatest unconstrained distal-end-portion outer radius $R_{DU}$ is greater than greatest systolic outer radius $R_S$, such as at least 5% greater than, e.g., as at least 15% greater than, and/or at least 2 mm greater than, no more than 10 mm greater than, or between 2 and 10 mm greater than greatest systolic outer radius $R_S$; and/or a greatest unconstrained proximal-end-portion outer radius $R_{PU}$ is greater than greatest systolic outer radius $R_S$, such as at least 5% greater than, e.g., at least 15% greater than, and/or at least 2 mm greater than, no more than 10 mm greater than, or between 2 and 10 mm greater than greatest systolic outer radius $R_S$.

In addition, greatest systolic outer radius $R_S$ is greater than greatest diastolic outer radius $R_D$ (e.g., at least 3% greater than, such as at least 5% greater than). For some applications, each of greatest unconstrained distal- and proximal-end-portion radii $R_{DU}$ and $R_{PU}$ is at least 5 mm, no more than 20 mm, and/or between 10 and 30 mm, e.g., at least 11 mm, no more than 25 mm, and/or between 11 and 25 mm.

In this configuration, endovascular stent-graft 20 may be deployed in an aneurysmatic blood vessel, such as an aneurysmatic aorta, such as described hereinabove with reference to FIGS. 1A-3C. Alternatively, endovascular stent-graft 20 may be deployed in a non-aneurysmatic blood vessel. In either case, the stent-graft may be configured to provide (passive, that is, by means of storage of mechanical energy) counterpulsation, by being configured to absorb and store blood pressure during systole and release and apply blood pressure during diastole. Counterpulsation is a technique for assisting the circulation by decreasing the afterload of the left ventricle and augmenting the diastolic pressure. Counterpulsation increases stroke volume by decreasing afterload, reduces heart workload, and maintains or increase coronary perfusion. Stent-graft 20 may thus be used, for example, for treating sclerotic disease in order to restore radial compliance of a blood vessel.

Figure 5:
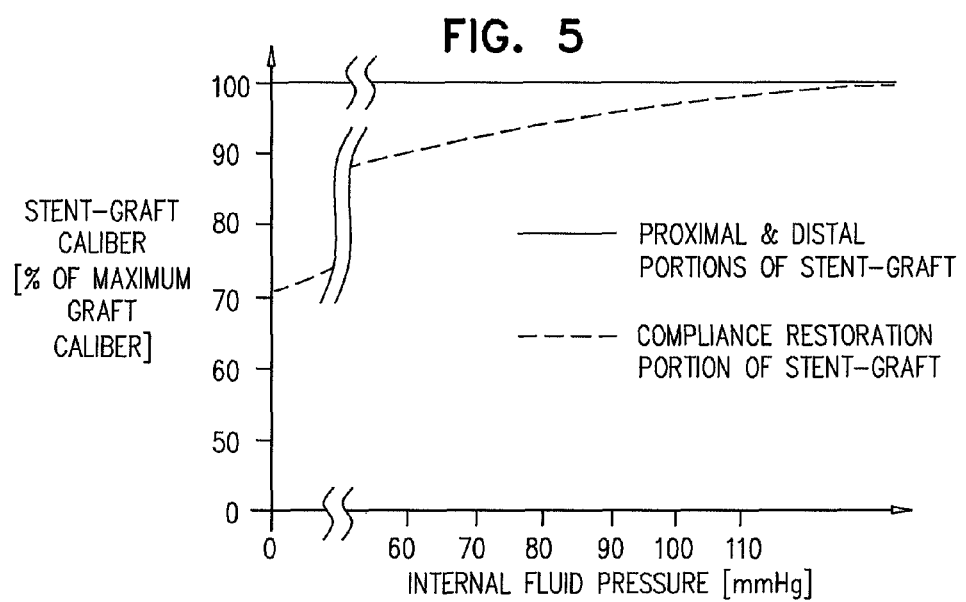
FIG. 5 is a graph that schematically illustrates the stent-graft caliber of a compliance-restoration body portion of the endovascular stent-graft of FIGS. 1A-4 vs. internal fluid pressure, in accordance with an application of the present invention.

Reference is now made to FIG. 5, which is a graph that schematically illustrates the stent-graft caliber of compliance-restoration body portion 34 vs. internal fluid pressure, in accordance with an application of the present invention. Stent-graft caliber of compliance-restoration body portion 34 is expressed as a percentage of maximum graft caliber (i.e., the graft caliber at burst pressure). As can be seen, while the caliber of distal and proximal portions 40 and 42 of body 22 of stent-graft 20 remain the same as internal fluid (e.g., blood) pressure increases and decreases, the caliber of compliance-restoration body portion 34 varies between about 70% and 100% of the maximum graft caliber as the internal fluid pressure changes.

In contrast, conventional stents-grafts that comprise polyethylene terephthalate (PET) or polytetrafluoroethylene (ePTFE, available under the trademark Gore-Tex®) maintain approximately 100% and 95%, respectively, of their maximum graft caliber as internal pressure varies in a physiologically-normal range. It is noted that even conventional stent-grafts that comprise graft material that allows a 5% change in graft caliber cannot increase by at least 5% in radius, because the stent elements of conventional stent-grafts are heat-set to hold the stent-graft in its maximum graft caliber even when not pressurized by physiological blood pressure from the inside.

Reference is now made to FIGS. 6-12B, which are schematic illustrations of a variable-length endovascular stent-graft 90, in accordance with respective applications of the present invention.

Figure 6:
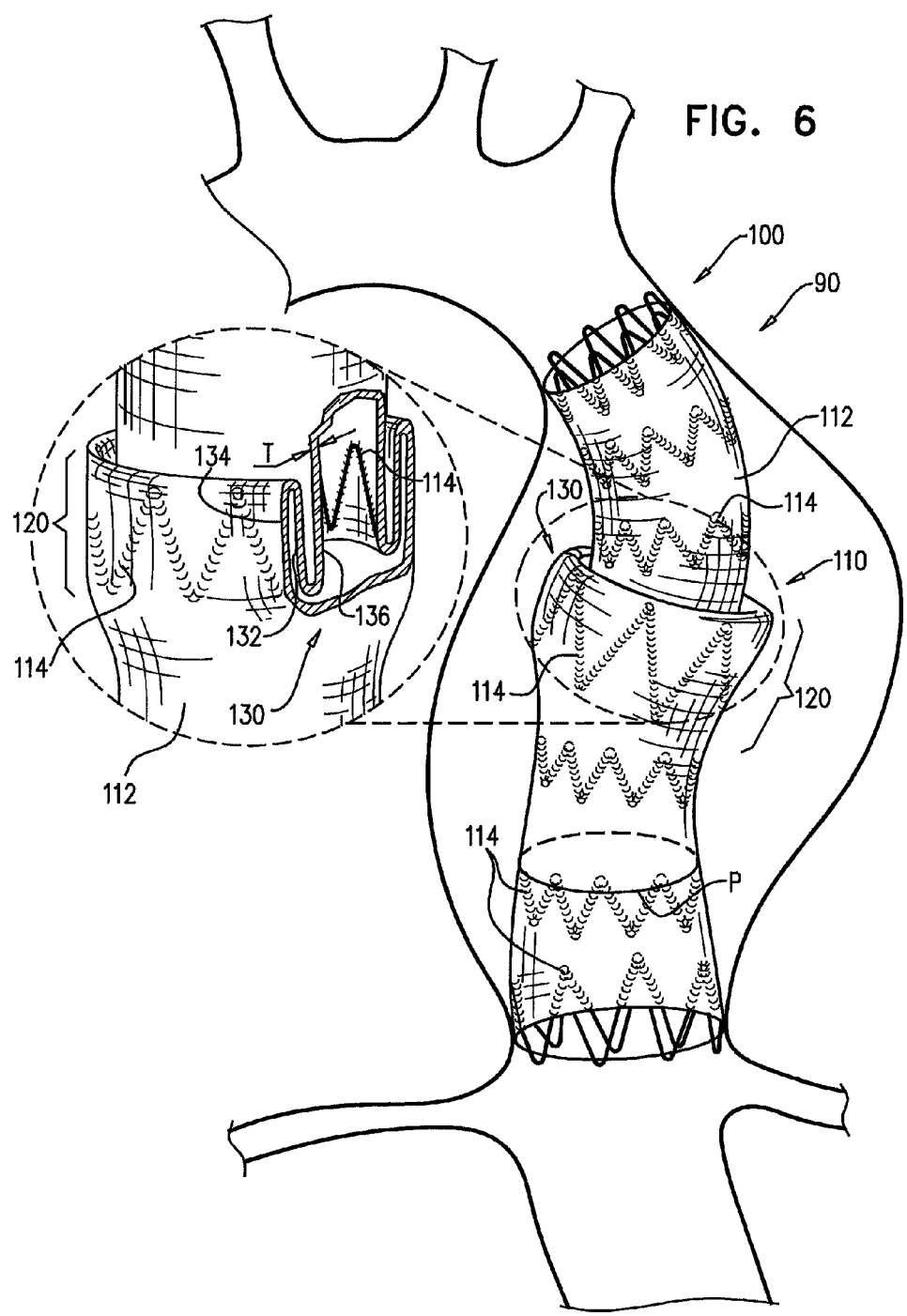
FIG. 6 is a schematic illustration of a variable-length stent-graft, in accordance with an application of the present invention.

Reference is made to FIG. 6, which is a schematic illustration of a variable-length stent-graft 100, in accordance with an application of the present invention. Variable-length stent-graft 100 is one implementation of variable-length-stent graft 90, described herein with reference to FIGS. 6-12B. Stent-graft 100 comprises a generally tubular body 110, which comprises a fluid flow guide 112 and a plurality of structural stent elements 114 attached to at least a portion of the fluid flow guide. Body 110 includes a variable-length section 120 that extends axially along a portion of body 110. Body 110, including variable-length section 120, is configured to assume a radially-compressed delivery state and a radially-expanded deployment state. Typically, body 110 is configured to self-expand from the delivery state to the deployment state upon being deployed from a delivery catheter. Body 110 is shown in FIGS. 6-12B in the radially-expanded deployment state.

Variable-length section 120, while radially-expanded in the deployment state, is configured to enable a change in an axial length thereof of at least 5 mm, such as at least 8 mm, e.g., at least 10 mm, and/or no more than 30 mm, e.g., no more than 25 mm. Alternatively or additionally, variable-length section 120 is configured such that the enabled change in the axial length is equal to at least 10%, e.g., at least 20%, and/or no more than 30%, e.g., no more than 10%, of outer diameter D of the fluid flow guide along the variable-length section when in its axially-shortest state ("greatest diameter" means the diameter at the longitudinal site having the greatest diameter). It is noted that even though the entire length of the stent-graft somewhat changes as the length of the variable-length section changes, the variable-length section should not be construed as including the entire length of the stent-graft. Instead, variable-length section 120 is to be understood as being that portion of the stent-graft that actually facilitates the change in axial length, as labeled in FIGS. 6-12B.

When body 110 is in the radially-expanded deployment state, variable-length section 120 is configured to assume an axially-shortest state thereof. Typically, at least when variable-length section 120 is in this axially-shortest state, one or more of structural stent elements 114 are arranged along the variable-length section such that the variable-length section has no structural-stent-element-free axial portions having axial lengths greater than 5%, e.g., greater than 10%, of greatest outer diameter D of the fluid flow guide along the variable-length section when in its axially-shortest state; for some applications, the variable-length section has no structural-stent-element-free portions when in its axially-shortest state. Typically, variable-length section 120 is configured such that structural stent elements 114 thereof do not undergo plastic deformation as the axial length changes.

Fluid flow guide 112 comprises a graft material, i.e., at least one biologically-compatible substantially blood-impervious flexible sheet. The flexible sheet may comprise, for example, a polyester, a polyethylene (e.g., a poly-ethylene-terephthalate), a polymeric film material (such as a fluoropolymer, e.g., polytetrafluoroethylene), a polymeric textile material (e.g., woven polyethylene terephthalate (PET)), natural tissue graft (e.g., saphenous vein or collagen), Polytetrafluoroethylene (PTFE), ePTFE, Dacron, or a combination of two or more of these materials. The graft material optionally is woven. Typically, the graft material is not accordion-pleated. For some applications, structural stent elements 114 comprise a metal. Alternatively or additionally, the structural stent elements comprise a self-expanding material, such that body 110 (and, optionally, stent-graft 90) is self-expandable. Alternatively or additionally, the structural stent elements comprise one or more metallic alloys, such as one or more superelastic metal alloys, a shape memory metallic alloy, and/or Nitinol.

For some applications, as shown in the blow-up in FIG. 6, variable-length stent-graft 100 is configured to define at least one generally tubular foldable section 130. For these applications, variable-length section 120 is configured to assume a folded position at least when variable-length section 120 is in the axially-shortest state. When the variable-length section is in which folded position, a first longitudinal subsection 132 of fluid flow guide 112 is radially sandwiched between second and third longitudinal subsections 134 and 136 of fluid flow guide 112. The variable-length section is typically configured to gradually unfold as the axial length thereof increases. In the folded position, second longitudinal subsection 134 radially surrounds the first longitudinal subsection 132, and first longitudinal subsection 132 radially surrounds third longitudinal subsection 136, such that first longitudinal subsection 132 is radially sandwiched between second and third longitudinal subsections 134 and 136. As a result, second subsection 134 at least partially longitudinally overlaps with both first and third longitudinal subsections 132 and 136.

For some applications, at least one of structural stent elements 114 is attached to second longitudinal subsection 134. Alternatively or additionally, for some applications, at least one of structural stent elements 114 is attached to third longitudinal subsection 136. Further alternatively or additionally, for some applications, an average surface coverage ratio of structural stent elements 114 on fluid flow guide 112 along first subsection 132 is no more than 20%, such as no more than 10%, of the greater of (a) an average surface coverage ratio on fluid flow guide 112 along second longitudinal subsection 134 and (b) an average surface coverage ratio on fluid flow guide 112 along third longitudinal subsection 136. For some applications, variable-length section 120 is configured such that none of structural stent elements 114 of body 110 is attached to first longitudinal subsection 132. This lower average surface coverage ratio (such as no surface coverage) provides greater evertibility to first longitudinal subsection 132, thereby enabling the transition of foldable section 130 from the folded state to the unfolded state. During this transition, first longitudinal subsection 132 is everted, i.e., turned inside-out.

Alternatively or additionally, the average surface coverage ratio of structural stent elements 114 on fluid flow guide 112 along first longitudinal subsection 132 is not necessarily no more than 20%. The greater evertibility of first longitudinal subsection 132 compared to second and third longitudinal subsections 134 and 136 may be provided by:
  configuring the structural stent elements along the first longitudinal subsection to be softer and/or thinner than the structural stent elements along the second and/or the third longitudinal subsections; and/or
  configuring the structural stent elements along the first longitudinal subsection to be longitudinally short, e.g., as simple circles disposed circumferentially around the stent-graft. Optionally, the structural stent elements extend around less than 360 degrees of the circumference of the stent-graft, i.e., are circumferentially incomplete, in order to increase the evertibility of the first longitudinal subsection.

For some applications, a first subgroup of structural stent elements 114 is attached (e.g., sutured) to second longitudinal subsection 134, and a second subgroup of structural stent elements 114 is attached (e.g., sutured) to third longitudinal subsection 136. For some applications, one of the first and second subgroups of structural stent elements 114 is attached (e.g., sutured) to an internal surface of fluid flow guide 112, and the other of the first and second subgroups is attached (e.g., sutured) to an external surface of fluid flow guide 112.

For some applications, as shown in FIG. 6, structural stent elements 114 are arranged as a plurality of generally circumferential bands. Longitudinal adjacent ones of the bands may or may not be joined to one another. For some applications, one or more of the circumferential bands is attached (e.g., sutured) to fluid flow guide 112 along second longitudinal subsection 134 (either to an external surface and/or to an internal surface thereof), and one or more of the circumferential bands is attached (e.g., sutured) to fluid flow guide 112 along third longitudinal subsection 136 (either to an external surface and/or to an internal surface thereof). Optionally, in addition, one or more of the circumferential bands is attached to fluid flow guide 112 along first longitudinal subsection 132 (either to an external surface and/or to an internal surface thereof).

For some applications, a surface coverage ratio of the one or more of structural stent elements 114 of variable-length section 120 on fluid flow guide 112 is at least 5%, such as at least 10%, when variable-length section 120 is the axially-shortest state when body 110 is in the radially-expanded deployment state.

For some applications, such as shown in the blow-up of FIG. 6, foldable section 130 comprises exactly three subsections, in which case the foldable section may be considered a triple-collar section. For other applications, foldable section 130 comprises more than three subsections, such as described with reference to FIG. 7 of above-mentioned U.S. Provisional Application 61/553,209, which is incorporated herein by reference.

Figure 7:
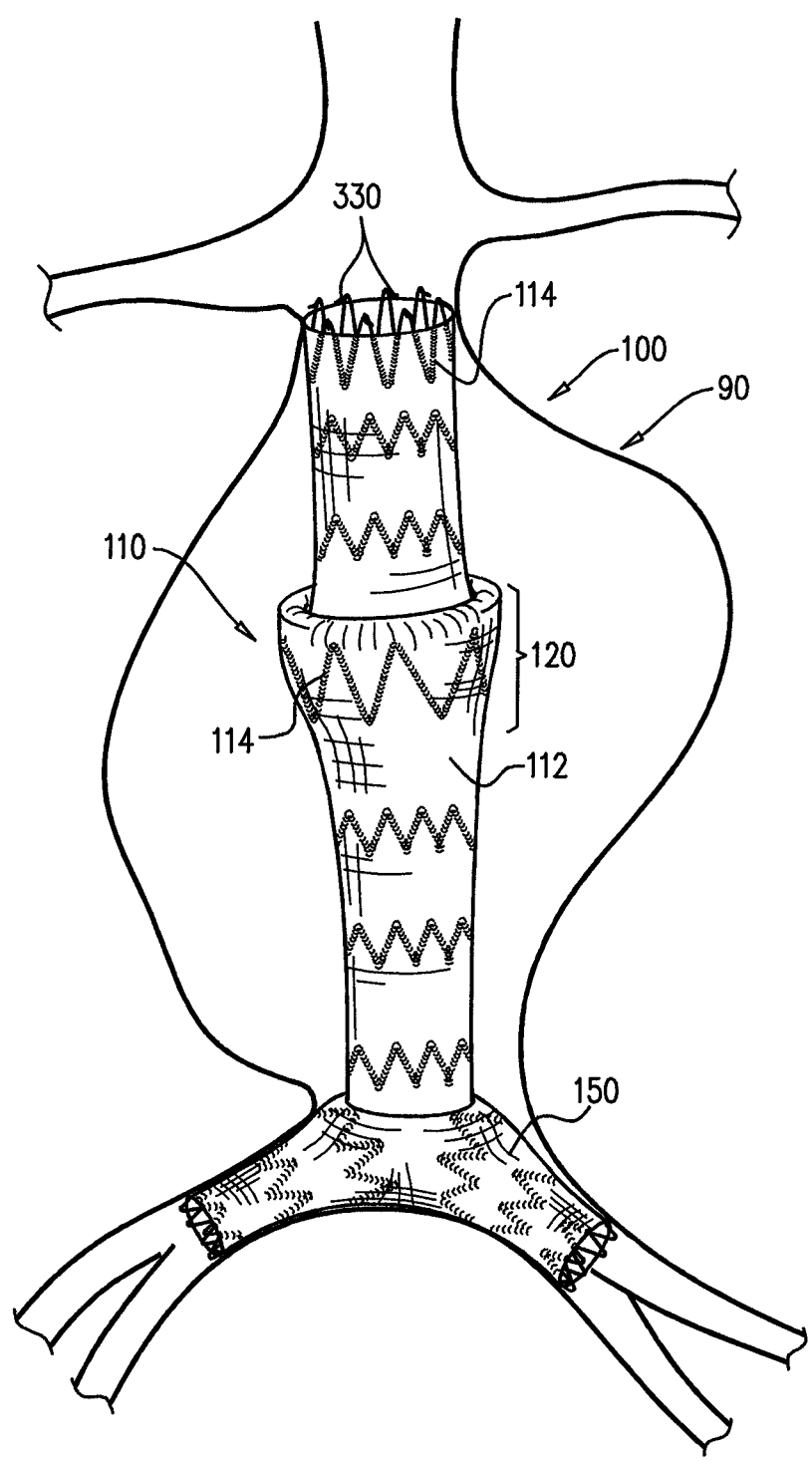
FIG. 7 is a schematic illustration of the variable-length stent-graft of FIG. 6 coupled to a bifurcated fixation stent-graft, in accordance with an application of the present invention.

Reference is now made to FIG. 7, which is a schematic illustration of variable-length stent-graft 100 coupled to a bifurcated fixation stent-graft 150, in accordance with an application of the present invention. In this configuration, bifurcated fixation stent-graft 150 facilitates long-term anchoring of variable-length stent-graft 100 at a bifurcation. For example, as shown, bifurcated fixation stent-graft 150 may comprise a bi-iliac self-expandable stent that is deployed in the iliac arteries, in order to facilitate long-term anchoring of stent-graft 100 at the aorto-iliac bifurcation. Stent-grafts 100 and 150 may be deployed and/or coupled to each other using techniques described in one or more of the following patent application publications, all of which are assigned to the assignee of the present application and are incorporated herein by reference: (a) PCT Publication WO 08/107885, (b) PCT Publication WO 2011/007354, (c) PCT Publication WO 2010/150208, e.g., with reference to FIGS. 14D-E, 20B, and/or 21B thereof, and (d) US Patent Application Publication 2011/0208289.

Figure 8A:
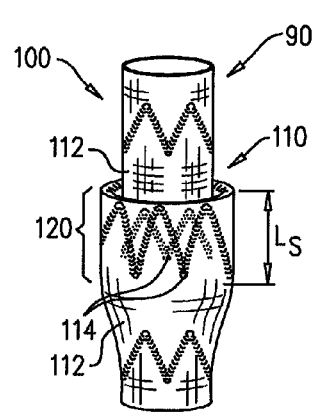
FIGS. 8A and 8B are schematic illustrations of the variable-length stent-graft of FIG. 6 in exemplary axially-shorter and axially-longer states, respectively, in accordance with an application of the present invention.
Figure 8B:
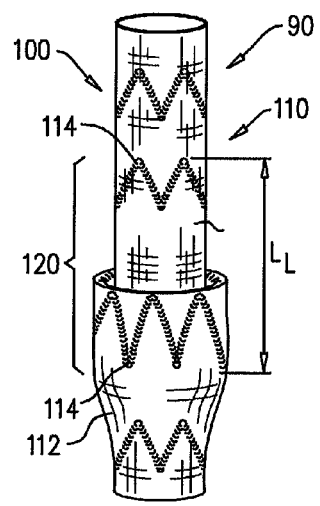

Reference is now made to FIGS. 8A and 8B, which are schematic illustrations of variable-length stent-graft 100 in exemplary axially-shorter and axially-longer states, respectively, in accordance with an application of the present invention. Stent-graft 100 is configured to assume a plurality of axially-shorter states (including the axially-shortest state described hereinabove with reference to FIG. 6). FIG. 8A shows stent-graft 100 in one of these axially-shorter states, in which variable-length section 120 has axial length Ls, and variable-length section 120 is in the folded position, as described hereinabove with reference to the blow-up of FIG. 6. FIG. 8B shows stent-graft 100 in one of the axially-longer states, in which variable-length section 120 has axial length $L_L$, and variable-length section 120 is nearly entirely unfolded. For some applications, the stent-graft may assume a slightly longer state, in which it is entirely unfolded (state not shown).

Reference is now made to FIGS. 9A-B and 10A-B, which are schematic illustrations of variable-length stent-grafts 200 and 202, in accordance with respective applications of the present invention. Variable-length stent-grafts 200 and 202 are respective implementations of variable-length-stent graft 90, described herein with reference to FIGS. 6-12B. Stent-grafts 200 and 202 comprise generally tubular body 110, which comprises fluid flow guide 112 and structural stent elements 114 attached to at least a portion of the fluid flow guide. Body 110 includes variable-length section 120 that extends axially along a portion of body 110. Body 110, including variable-length section 120, is configured to assume a radially-compressed delivery state and a radially-expanded deployment state. Body 110 is shown in FIGS. 9A-B and 10A-B in the radially-expanded deployment state.

Variable-length section 120 of stent-grafts 200 and 202 are configured to change length by means of rotation of a proximal end 206 of variable-length section 120 with respect to a distal end 208 of variable-length section 120. Such rotation causes structural elements 114 to twist. Variable-length section 120 shortens as structural elements 114 twist, and the graft material circumferentially folds around the more acutely curved structural elements.

For some applications, variable-length section 120 is configured to cyclically undergo an increase in the axial length that alternates with a decrease in the axial length. For some applications, the length of the variable-length section increase and decreases every heartbeat. For some applications, variable-section 120 shortens during diastole and lengthens during systole.

Figure 9A:
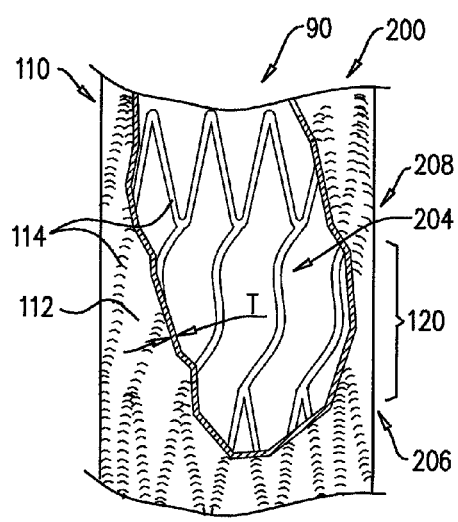
FIGS. 9A and 9B are schematic illustrations of additional variable-length stent-grafts, in accordance with respective applications of the present invention.

For some applications, as shown in FIGS. 9A and 10A-B, variable-length section 120 of stent-graft 200 is shaped so as to define, at least when the variable-length section is in the axially-shortest state, at least one single-sided helix 204, which comprises the one or more of structural elements 114. For some applications, variable-length section 120 is configured such that a step size of the at least one-single-sided helix increases as the axial length of the variable-length section increases.

Figure 9B:
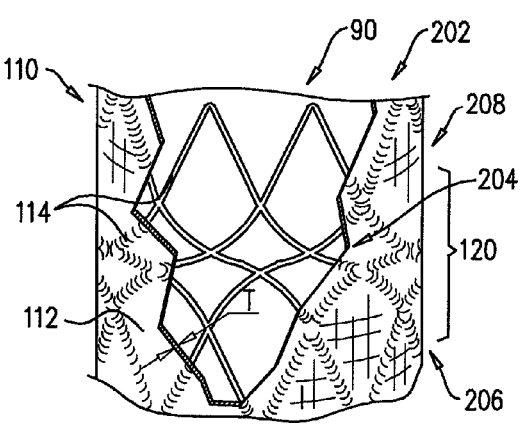

For some applications, as shown in FIG. 9B, variable-length section 120 of stent-graft 202 is shaped so as to define, at least when the variable-length section is in the axially-shortest state, at least one right-handed helix and at least one left-handed helix, which helices comprise the one or more of structural elements 114. For some applications, variable-length section 120 is configured such that respective step sizes of the right- and left-handed helices either both increase, or both decrease, as axial length of the variable-length section increases.

FIGS. 10A and 10B show variable-length stent-graft 200 of FIG. 9A in exemplary axially-shorter and axially-longer states, respectively. FIG. 10A shows stent-graft 200 in one of its axially-shorter states, in which variable-length section 120 has axial length $L_S$. Typically, variable-length section 120 is relaxed in the axially-shorter state. FIG. 10B shows stent-graft 200 in one of its axially-longer states, in which variable-length section 120 has axial length $L_L$. The one or more of structural stent elements 114 are configured to be elastically deformed at least when variable-length section 120 is in an axially-shortest of the axially-shorter states, such that the stent elements protrude radially outwardly (as shown in FIG. 10A) or radially inwardly (configuration not shown). Typically, the portions of these stent elements that protrude are attached (e.g., sutured) to fluid flow guide 112.

For configurations in which the stent elements protrude radially outward, variable-length section 120 is shaped so as to define, at least when the variable-length section is in the axially-shortest state, a radially-outward bulge 210 at least partially around a perimeter of an axial site on variable-length section 120. Radially-outward bulge 210 comprises the one or more of structural elements 114 of variable-length section 120, and, typically, a portion of the graft material of fluid flow guide 112. Typically, the variable-length section is configured such that a radial dimension of the bulge decreases as the axial length of the variable-length section increases. Typically, variable-length section 120 is configured such that structural stent elements 114 thereof do not undergo plastic deformation as the axial length changes.

Typically, when variable-length section 120 is in an axially-longest state (for example, as shown in FIG. 10B, and FIGS. 9A and 9B), the stent elements that define the bulge generally do not protrude radially outwardly or radially inwardly. The variable-length section, when in an axially-longest state, thus is not shaped so as to define bulge 210. Typically, structural elements 114 are relaxed in the axially-shortest state. For some applications, a surface coverage ratio of the one or more of structural stent elements 114 of variable-length section 120 on fluid flow guide 112 is at least 5%, such as at least 10%.

When body 110 is in the radially-expanded deployment state (as shown in FIGS. 9 and 10A-B), variable-length section 120 is configured to assume an axially-shortest state thereof (which might, for example, be the state shown in FIG. 10A). In this state the one or more of structural stent elements 114 are arranged along the variable-length section such that the variable-length section has no structural-stent-element-free axial portions having axial lengths greater than 5% of greatest outer diameter D of the fluid flow guide along the variable-length section when in its axially-shortest state. In this configuration, the variable-length section typically has no structural-stent-element free axial portions, when the variable-length section is in the axially-shortest state.

Figure 11:
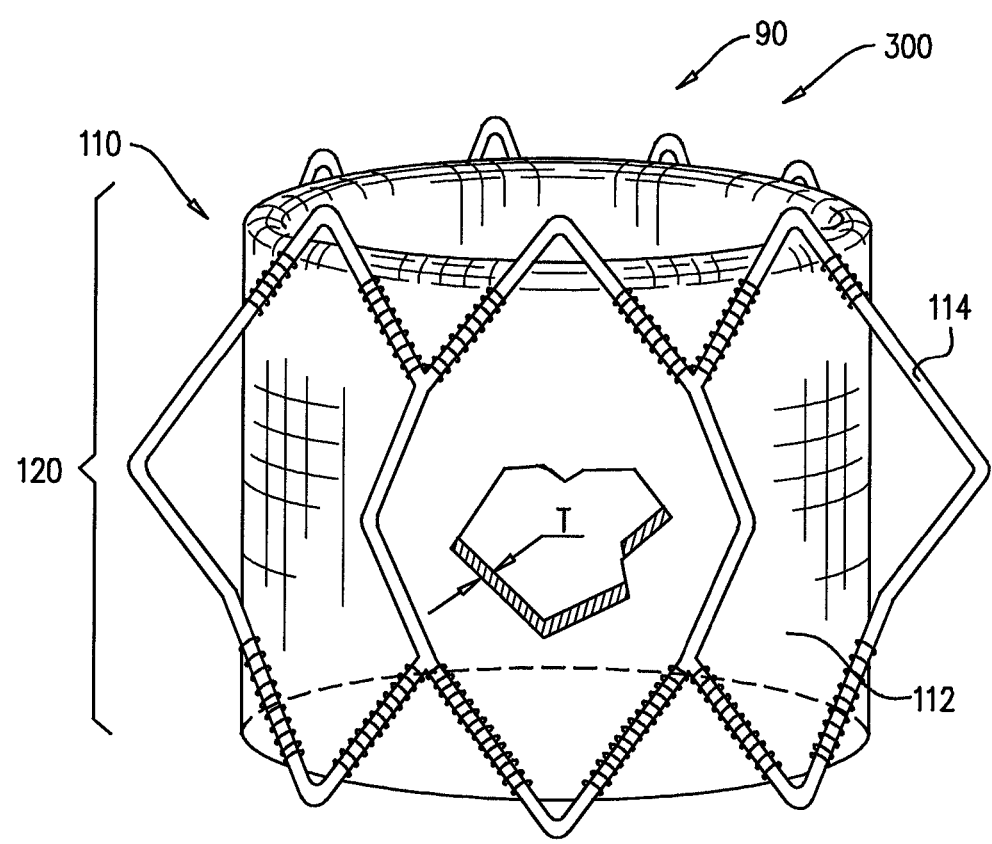
FIG. 11 is a schematic illustration of yet another variable-length stent-graft, in accordance with an application of the present invention.

Reference is made to FIGS. 11 and 12A-B, which are schematic illustrations of a variable-length stent-graft 300, in accordance with an application of the present invention. Variable-length stent-graft 300 is one implementation of variable-length-stent graft 90, described herein with reference to FIGS. 6-12B. Stent-graft 300 comprises generally tubular body 110, which comprises fluid flow guide 112 and structural stent elements 114 attached to at least a portion of the fluid flow guide. Body 110 includes variable-length section 120 that extends axially along a portion of body 110. Body 110, including variable-length section 120, is configured to assume a radially-compressed delivery state and a radially-expanded deployment state. Body 110 is shown in FIGS. 11 and 12A-B in the radially-expanded deployment state.

FIGS. 12A and 12B show variable-length stent-graft 300 in exemplary axially-shorter and axially-longer states, respectively. FIG. 12A shows stent-graft 300 in one of its axially-shorter states, in which variable-length section 120 has axial length $L_S$. Typically, variable-length section 120 is relaxed in the axially-shorter state. FIG. 12B shows stent-graft 300 in one of its axially-longer states, in which variable-length section 120 has axial length $L_L$. The one or more of structural stent elements 114 are configured to be elastically deformed at least when variable-length section 120 is in the axially-shortest state, such that the stent elements protrude radially outwardly (as shown in FIG. 10A) or radially inwardly (configuration not shown). Unlike the configuration shown in FIGS. 9 and 10A-B, in the configuration shown in FIGS. 11 and 12A-B the portions of the stent elements that protrude radially outward are not attached (e.g., sutured) to fluid flow guide 112. Typically, the graft material of fluid flow guide 112 along the variable-length section folds as the variable-length section axially shortens, as shown in FIG. 12A.

For configurations in which the stent elements protrude radially outward, variable-length section 120 is shaped so as to define, at least when the variable-length section is in the axially-shortest state, a radially-outward bulge 310 at least partially around a perimeter of an axial site on variable-length section 120. Radially-outward bulge 310 comprises the one or more of structural elements 114 of variable-length section 120. Typically, the variable-length section is configured such that a radial dimension of the bulge decreases as the axial length of the variable-length section increases. Typically, variable-length section 120 is configured such that structural stent elements 114 thereof do not undergo plastic deformation as the axial length changes.

Bulge 310 radially protrudes less when the variable-length section is in an axially-longer state than when in an axially-shorter state. Typically, variable-length section 120 is relaxed in the axially-shorter state. For some applications, a surface coverage ratio of the one or more of structural stent elements 114 of variable-length section 120 on fluid flow guide 112 is at least 5%, such as at least 10%.

When body 110 is in the radially-expanded deployment state (as shown in FIGS. 12A and 12B), variable-length section 120 is configured to assume an axially-shortest state thereof (which might, for example, be the state shown in FIG. 12A). In this state the one or more of structural stent elements 114 are arranged along the variable-length section such that the variable-length section has no structural-stent-element-free axial portions having axial lengths greater than 5% of greatest outer diameter D of the fluid flow guide along the variable-length section when in its axially-shortest state. In this configuration, the variable-length section typically has no structural-stent-element free axial portions, when the variable-length section is in the axially-shortest state.

Reference is made to FIGS. 9-10B and 11-12B. Alternatively, for some applications, variable-length section 120 is shaped so as to define, at least when the variable-length section is in the axially-shortest state, a radially-inward indentation at least partially around a perimeter of an axial site on the variable-length section. The indentation comprises the one or more of structural elements 114 of variable-length section 120. The variable-length section is configured such that a radial dimension of the indentation decreases as the axial length of the variable-length section increases. Typically, the variable-length section, when in an axially-longest state, is not shaped so as to define the indentation.

Reference is again made to FIGS. 6-12B. Typically, body 110 is configured such that elasticity of the graft material of fluid flow guide 112 provides less than 5%, such as less than 3% of a change in an axial length of variable-length section 120. In other words, the change in the axial length of variable-length section 120 is not primarily enabled by stretching of the graft material of the fluid flow guide. As a result, an average wall thickness T of the graft material (labeled in FIGS. 6, 9, and 11) does not decrease, or decreases only slightly, as the axial length increases. For some applications, during a 5 mm change in axial length of variable-length section 120, average wall thickness T of the graft material changes by no more than 15%, such as by no more than 10%.

Reference is still made to FIGS. 6-12B. For some applications, when body 110 is in the radially-expanded deployment state, variable-length section 120 is configured to undergo an increase in the axial length, and not a decrease in the axial length. For some applications, such an increase occurs gradually after implantation, such as over months or years, enabling variable-length endovascular stent-graft 90 to accommodate the gradual lengthening of the aorta that sometimes occurs. Such accommodation decreases the risk that the stent-graft might become dislodged and decreases the risk of endoleak.

Reference is still made to FIGS. 6-12B. For some applications, when body 110 is in the radially-expanded deployment state, variable-length section 120 is configured to cyclically undergo an increase in the axial length that alternates with a decrease in the axial length. For some applications, the length of the variable-length section increase and decreases every heartbeat. This repeated change in axial length provides axial compliance for reducing vascular resistance, similar to the radial compliance described above. For some applications, variable-section 120 shortens during diastole and lengthens during systole.

Reference is still made to FIGS. 6-12B. For some applications, when body 110 is in the radially-expanded deployment state, variable-length section 120 is configured to undergo the change in axial length in response to a change in fluid pressure within fluid flow guide 112, such as every heartbeat as pressure increases and decreases during systole and diastole. This repeated change in axial length provides axial compliance for reducing vascular resistance, similar to the radial compliance described above. Therefore, for these applications, the variable-length section typically is not configured to lock upon elongation.

For some applications in which structural stent elements 114 comprises a shape memory alloy, such as Nitinol, the spring-like properties of the alloy enable this repeated change in length of the variable-length section. Typically, variable-length section 120 is configured to undergo (a) an increase in the axial length in response to an increase in fluid pressure within the fluid flow guide, and (b) a decrease in the axial length in response to a decrease in the fluid pressure within the fluid flow guide. Alternatively, variable-length section 120 is configured to undergo (a) an increase in the axial length in response to a decrease in fluid pressure within the fluid flow guide, and (b) a decrease in the axial length in response to an increase in the fluid pressure within the fluid flow guide.

Reference is again made to FIG. 7. For some applications, stent-graft 90 further comprises one or more fixation members 330, such as barbs or hooks, located proximally and/or distally to variable-length section 120. The fixation members are configured to provide secured positioning between at least an end of the stent-graft and an internal circumference of the lumen. (Although fixation members 330 are shown only in FIG. 7, they may also be provided in the other configurations of stent-graft 90 described herein with reference to FIGS. 6 and 8A-12B.) For some applications, the fixation members are configured to provide secured positioning between at least an end of the stent-graft and an internal circumference of at least a branch of the lumen (e.g., a renal artery branching from the aorta). For example, the fixation members may comprises atraumatic arms that are configured to extend into the branch. For some applications, fixation members are configured to provide secured positioning between at least an end of the stent-graft and an external or internal circumference of another tubular stent-graft, e.g., are configured to allow telescopic anchoring of stent-graft 90 inside another stent-graft.

Figure 13:
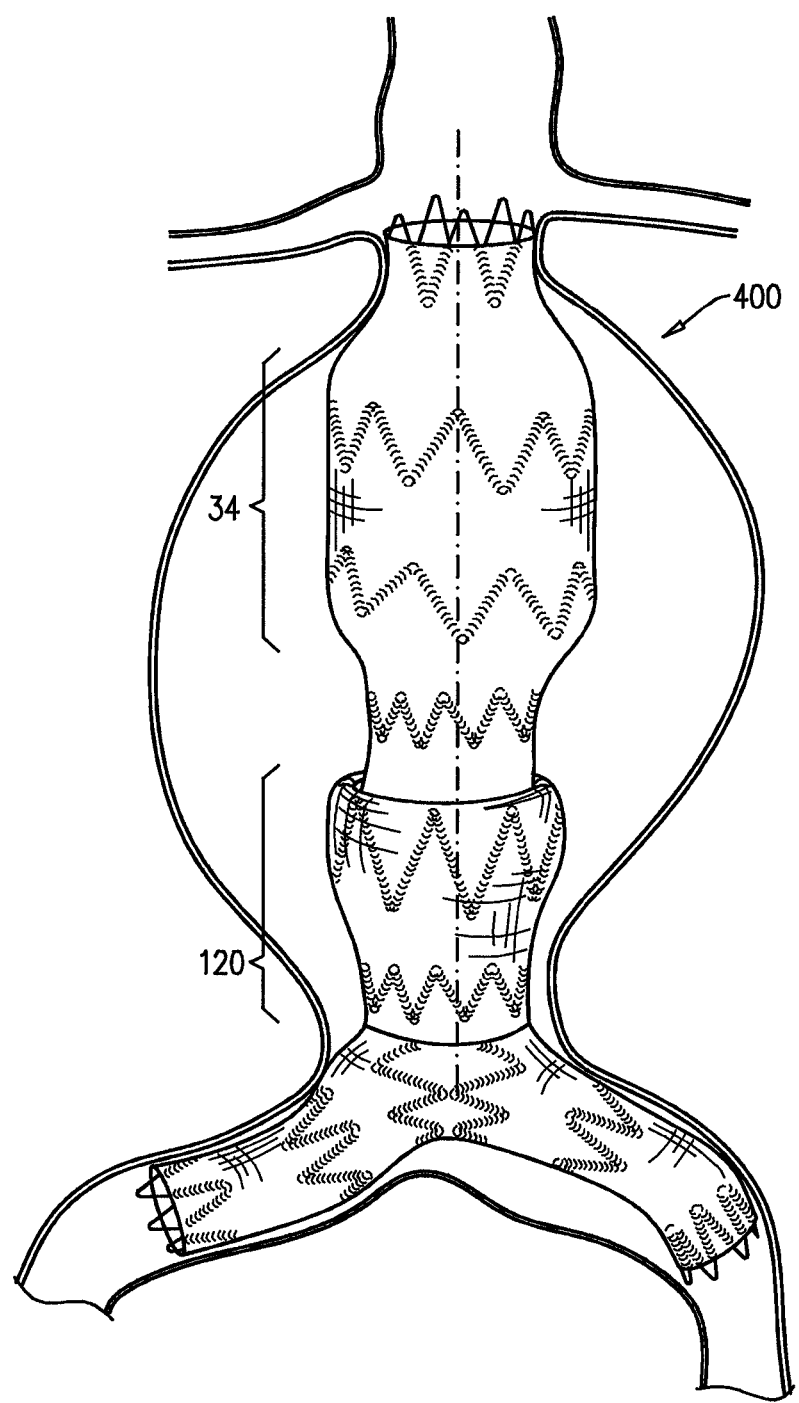
FIG. 13 is a schematic illustration of another stent-graft, which combines certain features of the stent-grafts of FIGS. 1A-B and 6, in accordance with an application of the present invention.

Reference is now made to FIG. 13, which is a schematic illustration of a stent-graft 400, in accordance with an application of the present invention. Stent-graft 400 combines certain features of stent-graft 20, described hereinabove with reference to FIGS. 1A-5, and certain features of stent-graft 90, described hereinabove with reference to FIGS. 6-12B. Stent-graft 400 includes both compliance-restoration body portion 34 and variable-length section 120. Stent-graft 400 thus provides both the axial and radial compliance described hereinabove.

Stent-graft 400 may implement the configuration of compliance-restoration body portion 34 described hereinabove with reference to FIGS. 1A-B (as shown in FIG. 13), or any of the other configurations of compliance-restoration body portion 34 described hereinabove with reference to FIGS. 2A-4. Similarly, stent-graft 400 may implement the configuration of variable-length section 120 described hereinabove with reference to FIGS. 6, 7, and 8A-B (as shown in FIG. 13), or any of the other configurations of variable-length section 120 described hereinabove with reference to 9-12B.

As used in the present application, including in the claims, "tubular" means having the form of an elongated hollow object that defines a conduit therethrough. A "tubular" structure may have varied cross-sections therealong, and the cross-sections are not necessarily circular. For example, one or more of the cross-sections may be generally circular, or generally elliptical but not circular, or circular.

The scope of the present invention includes embodiments described in the following applications, which are assigned to the assignee of the present application and are incorporated herein by reference. In an embodiment, techniques and apparatus described in one or more of the following applications are combined with techniques and apparatus described herein:

PCT Application PCT/IL2008/000287, filed Mar. 5, 2008, which published as PCT Publication WO 2008/107885 to Shalev et al., and U.S. application Ser. No. 12/529,936 in the national stage thereof, which published as US Patent Application Publication 2010/0063575 to Shalev et al.

U.S. Provisional Application 60/892,885, filed Mar. 5, 2007

PCT Application PCT/IL2007/001312, filed Oct. 29, 2007, which published as PCT Publication WO/2008/053469 to Shalev, and U.S. application Ser. No. 12/447,684 in the national stage thereof, which published as US Patent Application Publication 2010/0070019 to Shalev U.S. Provisional Application 60/991,726, filed Dec. 2, 2007

PCT Application PCT/IL2008/001621, filed Dec. 15, 2008, which published as PCT Publication WO 2009/078010, and U.S. application Ser. No. 12/808,037 in the national stage thereof, which published as US Patent Application Publication 2010/0292774

U.S. Provisional Application 61/219,758, filed Jun. 23, 2009

U.S. Provisional Application 61/221,074, filed Jun. 28, 2009

PCT Application PCT/IB2010/052861, filed Jun. 23, 2010, which published as PCT Publication WO 2010/150208, and U.S. application Ser. No. 13/380,278 in the national stage thereof, which published as US Patent Application Publication 2012/0150274

PCT Application PCT/IL2010/000549, filed Jul. 8, 2010, which published as PCT Publication WO 2011/004374

PCT Application PCT/IL2010/000564, filed Jul. 14, 2010, which published as PCT Publication WO 2011/007354, and U.S. application Ser. No. 13/384,075 in the national stage thereof, which published as US Patent Application Publication 2012/0179236

PCT Application PCT/IL2010/000917, filed Nov. 4, 2010, which published as PCT Publication WO 2011/055364

PCT Application PCT/IL2010/000999, filed Nov. 30, 2010, which published as PCT Publication WO 2011/064782

PCT Application PCT/IL2010/001018, filed Dec. 2, 2010, which published as PCT Publication WO 2011/067764

PCT Application PCT/IL2010/001037, filed Dec. 8, 2010, which published as PCT Publication WO 2011/070576

PCT Application PCT/IL2010/001087, filed Dec. 27, 2010, which published as PCT Publication WO 2011/080738

PCT Application PCT/IL2011/000135, filed Feb. 8, 2011, which published as PCT Publication WO 2011/095979

PCT Application PCT/IL2011/000801, filed Oct. 10, 2011, which published as PCT Publication WO 2012/049679

U.S. application Ser. No. 13/031,871, filed Feb. 22, 2011, which published as US Patent Application Publication 2011/0208289

U.S. Provisional Application 61/496,613, filed Jun. 14, 2011

U.S. Provisional Application 61/505,132, filed Jul. 7, 2011

U.S. Provisional Application 61/529,931, filed Sep. 1, 2011

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising an endovascular stent-graft, which comprises a generally tubular body, which body (a) is configured to assume a radially-compressed delivery state and a radially-expanded deployment state, and (b) comprises:
a flexible stent member; and
a tubular fluid flow guide, which comprises a graft material, and is attached to the stent member, the graft material comprising one or more of the following materials: a polyester, a polyethylene, a polymeric film material, a polymeric textile material, woven polyethylene terephthalate (PET), polytetrafluoroethylene (PTFE), ePTFE, a woven graft material, and a medical-grade textile,
wherein the body includes a compliance-restoration body portion, which extends axially along a portion of the body, and which comprises a portion of the stent member and a portion of the fluid flow guide,
wherein, when the body is in the radially-expanded deployment state, the compliance-restoration body portion, including the portion of the stent member, is (a) configured to assume a greatest diastolic outer radius when the body is internally pressurized by fluid having a pressure of 80 mmHg, and (b) configured to assume a greatest systolic outer radius when the body is internally pressurized by fluid having a pressure of 120 mmHg, and
wherein the greatest systolic outer radius is at least 5% greater than the greatest diastolic outer radius.

2. The apparatus according to claim 1, wherein the greatest systolic outer radius is at least 10% greater than the greatest diastolic outer radius.

3. The apparatus according to claim 1, wherein the stent member is heat-set to cause the compliance-restoration body portion to assume the greatest diastolic outer radius when the body is internally pressurized by the fluid having the pressure of 80 mmHg.

4. The apparatus according to claim 1, wherein, when the body is in the radially-expanded deployment state, the compliance-restoration body portion is configured to assume a greatest relaxed outer radius when the body is not internally pressurized by fluid, which greatest relaxed outer radius is no more than 95% of the greatest diastolic outer radius.

5. The apparatus according to claim 4, wherein the stent member is heat-set to cause the compliance-restoration body portion to assume the greatest relaxed outer radius when unconstrained.

6. The apparatus according to claim 1, wherein the fluid flow guide alone is configured to assume first and second perimeters when internally pressurized by fluid having a pressure of 80 and 120 mmHg, respectively, the second perimeter being no more than 10% greater than the first perimeter.

7. The apparatus according to claim 1, wherein the fluid flow guide alone is configured to assume first and second perimeters when internally pressurized by fluid having a pressure of 80 and 120 mmHg, respectively, the second perimeter being between 0.5% and 5% greater than the first perimeter.

8. The apparatus according to claim 1, wherein the greatest systolic outer radius is no more than 30% greater than the greatest diastolic outer radius.

9. The apparatus according to claim 1, wherein the greatest diastolic outer radius is between 7.5 mm and 25 mm, when the body is in the radially-expanded deployment state.

10. The apparatus according to claim 1, wherein the greatest systolic outer radius is between 8.5 mm and 30 mm, when the body is in the radially-expanded deployment state.

11. The apparatus according to claim 1, wherein the body further includes distal and proximal portions, wherein the compliance-restoration body portion is disposed longitudinally between the distal portion and the proximal portion, and wherein respective greatest radii of the distal and the proximal portions are each at least 5% greater than a greatest relaxed outer radius of the compliance-restoration body portion, when the body is unconstrained in the radially-expanded deployment state.

12. The apparatus according to claim 1, wherein the body further includes distal and proximal portions, wherein the compliance-restoration body portion is disposed longitudinally between the distal portion and the proximal portion, and wherein respective greatest radii of the distal and the proximal portions are each at least 5% greater than the greatest diastolic outer radius, when the body is in the radially-expanded deployment state.

13. The apparatus according to claim 1, wherein the body further includes distal and proximal portions, wherein the compliance-restoration body portion is disposed longitudinally between the distal portion and the proximal portion, and wherein a greatest outer radius of the distal portion, when unconstrained, is between 2 and 10 mm greater than the greatest systolic outer radius, when the body is in the radially-expanded deployment state.

14. Apparatus comprising an endovascular stent-graft, which comprises a generally tubular body, which body (a) is configured to assume a radially-compressed delivery state and a radially-expanded deployment state, and (b) comprises:
 a flexible stent member; and
 a tubular fluid flow guide, which comprises a graft material, and is attached to the stent member,
 wherein the body includes a compliance-restoration body portion, which extends axially along a portion of the body, and which comprises a portion of the stent member and a portion of the fluid flow guide,
 wherein, when the body is in the radially-expanded deployment state, the compliance-restoration body portion, including the portion of the stent member, is (a) configured to assume a greatest diastolic outer radius when the body is internally pressurized by fluid having a pressure of 80 mmHg, and (b) configured to assume a greatest systolic outer radius when the body is internally pressurized by fluid having a pressure of 120 mmHg,
 wherein the greatest systolic outer radius is at least 5% greater than the greatest diastolic outer radius,
 wherein the graft material of the fluid flow guide of the compliance-restoration body portion is shaped so as to be expandable to a maximum greatest outer radius, and
 wherein the maximum greatest outer radius of the graft material of the fluid flow guide of the compliance-restoration body portion is equal to the greatest systolic outer radius of the compliance-restoration body portion, such that the compliance-restoration body portion is limited by the graft material of the fluid flow guide from assuming an outer radius that is greater than the maximum greatest outer radius.

15. The apparatus according to claim 14, wherein the flexible stent member is attached to an internal surface of the tubular fluid flow guide.

16. The apparatus according to claim 14, wherein the flexible stent member comprises a plurality of structural stent elements, and wherein a portion of the structural stent elements are attached to an internal surface of the fluid flow guide, and another portion of the structural stent elements are attached to an external surface of the fluid flow guide.

17. Apparatus comprising an endovascular stent-graft, which comprises a generally tubular body, which body (a) is configured to assume a radially-compressed delivery state and a radially-expanded deployment state, and (b) comprises:
 a flexible stent member; and
 a tubular fluid flow guide, which comprises a graft material, and is attached to the stent member,
 wherein the body includes a compliance-restoration body portion, which extends axially along a portion of the body, and which comprises a portion of the stent member and a portion of the fluid flow guide,
 wherein, when the body is in the radially-expanded deployment state, the compliance-restoration body portion, including the portion of the stent member, is (a) configured to assume a greatest diastolic outer radius when the body is internally pressurized by fluid having a pressure of 80 mmHg, and (b) configured to assume a greatest systolic outer radius when the body is internally pressurized by fluid having a pressure of 120 mmHg,
 wherein the greatest systolic outer radius is at least 5% greater than the greatest diastolic outer radius, and
 wherein the graft material of the portion of the fluid flow guide is at least partially folded when the body is in the radially-expanded deployment state and is internally pressurized by the fluid having the pressure of 80 mmHg.

18. Apparatus comprising an endovascular stent-graft, which comprises a generally tubular body, which body (a) is configured to assume a radially-compressed delivery state and a radially-expanded deployment state, and (b) comprises:
 a flexible stent member; and
 a tubular fluid flow guide, which comprises a graft material, and is attached to the stent member,
 wherein the body includes a compliance-restoration body portion, which extends axially along a portion of the body, and which comprises a portion of the stent member and a portion of the fluid flow guide,
 wherein, when the body is in the radially-expanded deployment state, the compliance-restoration body portion, including the portion of the stent member, is (a) configured to assume a greatest diastolic outer radius when the body is internally pressurized by fluid having a pressure of 80 mmHg, and (b) configured to assume a greatest systolic outer radius when the body is internally pressurized by fluid having a pressure of 120 mmHg,
 wherein the greatest systolic outer radius is at least 5% greater than the greatest diastolic outer radius, and
 wherein the body further includes distal and proximal portions, and wherein the compliance-restoration body portion is disposed longitudinally between the distal portion and the proximal portion, wherein, when the body is in the radially-expanded deployment state, the distal and proximal portions are (a) configured to assume greatest diastolic distal- and proximal-end-portion radii, respectively, when the body is internally pressurized by fluid having a pressure of 80 mmHg, and (b) configured to assume greatest systolic distal- and proximal-end-portion radii, respectively, when the body is internally pressurized by fluid having a pressure of 120 mmHg, wherein the greatest systolic distal-end-portion outer radius is less than 2% greater than the greatest diastolic distal-end-portion outer radius, and wherein the greatest systolic proximal-end-portion outer radius is less than 2% greater than the greatest diastolic proximal-end-portion outer radius.

* * * * *